US006926681B1

(12) United States Patent
Ramey et al.

(10) Patent No.: US 6,926,681 B1
(45) Date of Patent: *Aug. 9, 2005

(54) METHOD AND SYSTEM FOR PERFORMING MICROABRASION AND SUCTION MASSAGE

(75) Inventors: John S. Ramey, Orem, UT (US); Larry K. Beardall, Sandy, UT (US); Eric M. Simon, Salt Lake City, UT (US); Randall D. Block, Salt Lake City, UT (US)

(73) Assignee: Dynatronics Corporation, Salt Lake City, UT (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/009,932

(22) PCT Filed: May 11, 2000

(86) PCT No.: PCT/US00/13085

§ 371 (c)(1),
(2), (4) Date: May 24, 2002

(87) PCT Pub. No.: WO00/67692

PCT Pub. Date: Nov. 16, 2000

Related U.S. Application Data

(63) Continuation-in-part of application No. 09/514,531, filed on Feb. 28, 2000, now Pat. No. 6,582,442, and a continuation-in-part of application No. 09/309,958, filed on May 11, 1999, now abandoned.

(51) Int. Cl.[7] .................... A61H 23/04; A61B 17/50
(52) U.S. Cl. ................... 601/6; 601/7; 606/131; 604/315
(58) Field of Search ............... 606/131, 167, 606/133; 601/6, 7, 9, 10; 604/313, 315

(56) References Cited

U.S. PATENT DOCUMENTS

| 554,299 | A | * | 2/1896 | Parker | ............... 451/100 |
| 2,238,541 | A | * | 4/1941 | Spagnolo | ............... 15/397 |

(Continued)

FOREIGN PATENT DOCUMENTS

| CH | 168279 | 6/1934 | ............... 601/6 |
| DE | 532086 | 8/1931 | ............... 601/6 |

(Continued)

OTHER PUBLICATIONS

Angel Healing, Inc. product brochure, "Dare to be Beautiful," Milpitas, California.

(Continued)

*Primary Examiner*—Danton DeMille
(74) *Attorney, Agent, or Firm*—Berne S. Broadbent; Kirton & McConkie

(57) ABSTRACT

Massage device (10) comprising head (12), which 76 defines cavity (8) and an opening to cavity (8). Head (12) has one or more contact surfaces and post (32) connected to head (12). Post (32) is positioned within cavity (8) and extends toward the opening. Post (32) also has one or more contact surfaces. Vacuum source (49) communicating with cavity (8) provides a means for creating negative pressure with cavity (8). Additionally, a method and system for performing abrasion on a surface, such as on the skin 74 of a patient, is disclosed. The dermabrasion apparatus includes means for delivering and retrieving material to and from a selected site to be abraded, a delivery and retrieval hand piece, an abrasive handling device, and a waste retrieval holding device. Hand piece (118) is coupled to the abrasive handling device as well as the waste retrieval holding device, which is further coupled to the delivery and retrieval means.

43 Claims, 10 Drawing Sheets

U.S. PATENT DOCUMENTS

| | | | |
|---|---|---|---|
| 2,608,032 A | 8/1952 | Garver | 51/11 |
| 2,921,585 A | 1/1960 | Schumann | 128/355 |
| 3,085,573 A | 4/1963 | Meyer et al. | 128/240 |
| 3,297,024 A | 1/1967 | Robinson | 128/38 |
| 3,543,444 A | 12/1970 | Mehta | 51/8 |
| 3,574,239 A | 4/1971 | Sollerud | 4/1 |
| 3,715,838 A | 2/1973 | Young et al. | 51/12 |
| 3,760,800 A | 9/1973 | Staffin et al. | 128/24.1 |
| 3,841,322 A | 10/1974 | Spelio | 128/40 |
| 3,841,323 A | 10/1974 | Stoughton | 128/40 |
| 4,090,334 A | 5/1978 | Kurowski et al. | 51/427 |
| 4,214,576 A | 7/1980 | Henley | 128/24.1 |
| 4,333,277 A | 6/1982 | Tasedan | 51/425 |
| 4,375,740 A | 3/1983 | Brown | 51/425 |
| 4,445,517 A | 5/1984 | Feild | 128/752 |
| 4,498,462 A | 2/1985 | Henley | 128/24.1 |
| 4,516,398 A | 5/1985 | Wuchinich | 604/22 |
| 4,531,934 A | 7/1985 | Kossovsky et al. | 604/22 |
| 4,560,373 A | 12/1985 | Sugino et al. | 604/30 |
| 4,578,058 A | 3/1986 | Grandon | 604/27 |
| 4,583,530 A | 4/1986 | Henley | 128/65 |
| 4,646,480 A | 3/1987 | Williams | 51/424 |
| 4,674,239 A | 6/1987 | Jodoin | 51/424 |
| 4,676,749 A | 6/1987 | Mabille | 433/88 |
| 4,729,368 A | 3/1988 | Guitay | 128/57 |
| 4,757,814 A | 7/1988 | Wang et al. | 128/318 |
| 4,883,047 A | 11/1989 | Guitay | 128/38 |
| 4,966,609 A | 10/1990 | Callinan et al. | 51/295 |
| 5,037,431 A | 8/1991 | Summers et al. | 606/131 |
| 5,037,432 A | 8/1991 | Molinari | 606/131 |
| 5,080,656 A | 1/1992 | Martz et al. | 604/289 |
| 5,100,412 A | 3/1992 | Rosso | 606/131 |
| 5,152,281 A | 10/1992 | Koll | 128/57 |
| 5,207,234 A | 5/1993 | Rosso | 128/898 |
| 5,215,078 A | 6/1993 | Fulop | 128/52 |
| 5,322,504 A | 6/1994 | Doherty et al. | 606/167 |
| 5,330,354 A | 7/1994 | Gallant | 433/88 |
| 5,334,016 A | 8/1994 | Goldsmith et al. | 433/29 |
| 5,334,019 A | 8/1994 | Goldsmith et al. | 433/88 |
| 5,350,299 A | 9/1994 | Gallant | 433/88 |
| 5,423,803 A | 6/1995 | Tankovich et al. | 606/9 |
| 5,484,283 A | 1/1996 | Franetzki | 433/116 |
| 5,489,291 A | 2/1996 | Wiley | 606/170 |
| 5,525,058 A | 6/1996 | Gallant et al. | 433/88 |
| 5,562,643 A | 10/1996 | Johnson | 604/290 |
| 5,665,053 A | 9/1997 | Jacobs | 601/2 |
| 5,681,026 A | 10/1997 | Durand | 125/129.16 |
| 5,752,829 A | 5/1998 | Goldsmith et al. | 433/88 |
| 5,765,759 A | 6/1998 | Bruns et al. | 239/398 |
| 5,795,626 A | 8/1998 | Gabel et al. | 427/458 |
| 5,800,446 A | 9/1998 | Banuchi | 606/131 |
| 5,810,842 A | 9/1998 | Di Fiore et al. | 606/131 |
| 5,885,211 A | 3/1999 | Eppstein et al. | 600/309 |
| 5,971,999 A | 10/1999 | Naldoni | 606/131 |
| 6,012,975 A | 1/2000 | Jager | 451/87 |
| 6,139,554 A | 10/2000 | Karkar et al. | 606/131 |
| D441,863 S | 5/2001 | Khalaj et al. | D24/133 |
| 6,235,039 B1 | 5/2001 | Parkin et al. | 606/131 |
| 6,241,739 B1 | 6/2001 | Waldron | 606/131 |

FOREIGN PATENT DOCUMENTS

| | | | |
|---|---|---|---|
| DE | 201229 | 12/1958 | |
| DE | 2218370 | 9/1973 | 601/6 |
| DE | 2742058 A1 | 3/1979 | |
| DE | 3421390 A1 | 12/1985 | |
| DE | 234608 A1 | 4/1986 | |
| DE | 3535571 A1 | 5/1987 | 601/6 |
| DE | 4102684 A1 | 8/1992 | |
| DE | 9215436 | 3/1994 | |
| EP | 0035040 A1 | 9/1981 | |
| EP | 0143617 A2 | 6/1985 | |
| EP | 0258901 A2 | 3/1988 | |
| EP | 0564392 A2 | 10/1993 | |
| EP | 0806184 A1 | 11/1997 | |
| FR | 638309 | 5/1928 | 601/6 |
| FR | 1109131 | 1/1956 | 601/6 |
| FR | 1136127 | 5/1957 | 601/6 |
| FR | 1501054 | 11/1967 | 601/6 |
| FR | 2057514 | 5/1971 | 601/6 |
| IT | 553076 | 12/1956 | |
| IT | 1184922 | 10/1987 | |
| NO | 50247 | 2/1932 | 601/6 |
| SE | 152189 | 11/1955 | 601/6 |
| SU | 1556676 A1 | 4/1990 | 601/6 |
| WO | WO 96/03959 | 2/1996 | |
| WO | WO 97/11650 | 4/1997 | |
| WO | WO 99/07439 | 2/1999 | |
| WO | WO 99/20336 | 4/1999 | |
| WO | WO 99/23951 | 5/1999 | |
| WO | WO 00/67692 | 11/2000 | |

OTHER PUBLICATIONS

BHC Group web page, Dermabraze,: Jun. 1999, http://wwww.bhe-group.demon.co.uk/dermabra.html.

Cosmos Medical Technology, Inc., "EuroPeel Micro-Dermabrasion System" (U.S.A.).

Dynatronics Coporation product brochure, "Sinergie Lifestyle System," Salt Lake City, Utah, 1998.

Dynatronics Coporation product brochure, "Sinergie The Ultimate Cellulite solution," Salt Lake City, Utah, 1999.

Edge Systems Corporation product brochure, "Delphia II," Signal Hill, California.

Micro Dermabrasion International, "Skin-A-Peel" (U.S.A.).

Optical Technology, Inc. web page, "Derma Genesis," Jul. 1999 http://www.dermagenesis.com/main.html.

Pneumadyne web page, "Introducing the new Bleed Valve," Dec. 1998, http://www.pneumadyne.com/c-products.html.

Silhouet-Tone (U.S.A.) Ltd, "Micro Peel" (U.S.A.).

Slimtone USA, "Diamond Dermabrasion" (U.S.A.).

SMEI srl, "Skin System E" (Italy).

SoundSkin Corporation, "Smart Peel Skin Exfoliation System" (1998, U.S.A.).

* cited by examiner

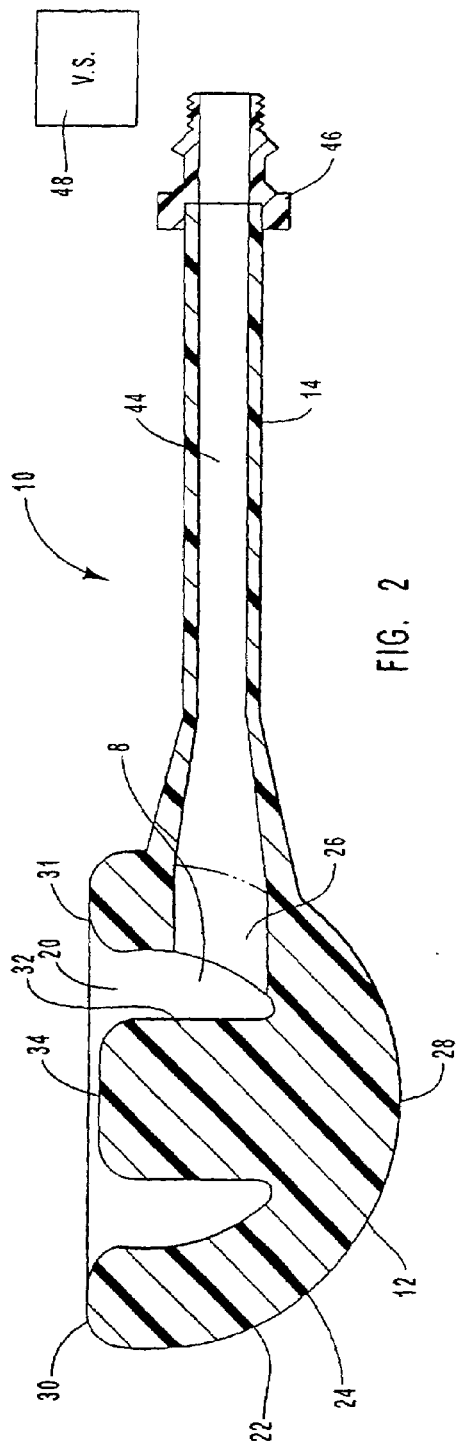
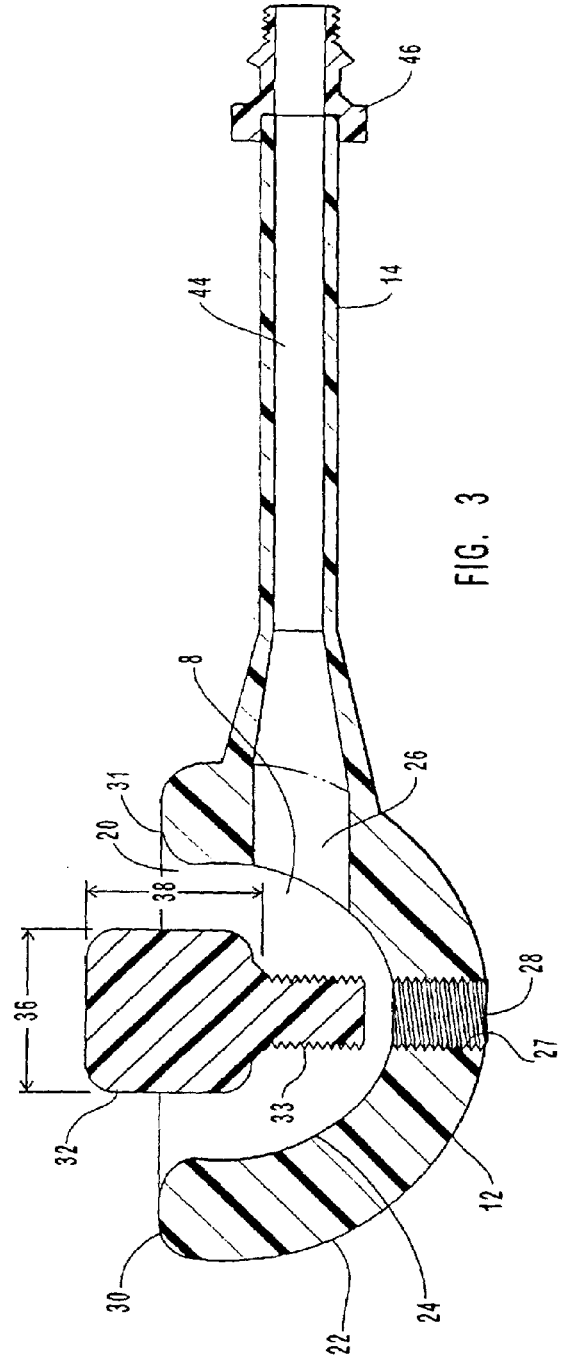
FIG. 2
FIG. 3

METHOD AND SYSTEM FOR PERFORMING MICROABRASION AND SUCTION MASSAGE

This is a 371 of PCT/US00/13085 filed May 11, 2000, which is a continuation-in-part of Ser. No. 09/309,958 filed May 11, 1999, now abandoned, and is a continuation-in-part of Ser. No. 09/514,531 filed Feb. 28, 2000, now U.S. Pat. No. 6,582,422.

BACKGROUND OF THE INVENTION

This invention relates to massage devices and methods and, more particularly, to novel apparatus and methods for use in providing aesthetic massages. Further still, the present invention relates generally to abrasion systems and methods for abrading a surface in a controlled manner and, more particularly, to a portable or adaptable microabrasion system that operates to perform dermabrasion in a controlled manner with improved efficiency, hygiene, and finish. The present invention also relates to a system and method that integrates both types of treatment in one convenient apparatus.

In the health and beauty industry there has been a great deal of interest in the use of massage and body contouring treatments for their therapeutic and cosmetic value. Massage and body contouring can provide such benefits as the increase of local blood circulation, and relief of minor muscle aches and pains. It has also been reported that such treatments may aid in reducing the appearance of cellulite, smoothing the skin and reducing girth. Moreover, patients find massage and body contouring treatments to be relaxing.

Traditionally massages are given by hand, usually by a masseuse who has received extensive training in various hand massage techniques. One technique known as petrissage is described as kneading, or lifting and rolling of the skin. For example, to perform the petrissage technique, the skin and surface muscles of the person receiving the massage can be gently grasped between the thumb and fingers with a pinching-like motion. Petrissage is reported as being stimulating to muscles and to circulation of the deeper blood vessels and lymphatics. Another hand massage technique called effleurage is described as a long, gliding or stroking, movement on the surface of the skin, often using, the entire, flat surface of the hand to stroke the skin. Effleurage is a soothing technique and is reported as increasing circulation and relaxation in patients. Other massage techniques include friction, tapotement, and vibration.

Massage treatments given by hand can be costly for the patient and tiring for the masseuse. In addition, manual manipulations are not typically capable of sustained massage of deep subdermal tissue layers. In an attempt to reduce the expense and effort required for hand massage, various mechanical massage and body contouring devices have been developed. These massage and body contouring devices imitate, to some degree, the manipulation of the skin, the direction or pattern of that manipulation and the pressure applied to the skin associated with various hand massage techniques. Thus, the aim of many massage and body contouring devices is to provide a patient with the same or similar type of massage as can be received by hand while reducing cost to the person receiving the treatment and reducing, the training and effort required of the person giving the treatment.

Prior art massage and body contouring devices employ various means for simulating massage techniques. For example, prior art devices attempt to simulate the kneading or lifting and rolling, of the skin experienced when a petrissage technique is used. Some of these prior art devices use a vacuum means for lifting the skin. Other prior art devices use various types of rollers to lift and knead the skin. The rollers are generally cylindrical in shape and may also be combined with other mechanical or vacuum means for lifting the skin. Other devices employ motorized or mechanically activated rollers which squeeze skin between the rollers.

U.S. Pat. No. 4,729,368 to Guitay discloses an apparatus for massaging the human body comprising in part "two parallel active rollers, preferably driven in rotation by a motor," the rollers are "mounted inside a manually operated housing."

U.S. Pat. No. 3,841,323 to Stoughton discloses a "massage apparatus by which pulsating air suction is applied to any selected area of the human body so as to stimulate circulation of the blood. The apparatus includes a bellows which is coupled to a suction cup through an elongated flexible tube."

U.S. Pat. No. 3,841,322 to Spelio discloses "a variable pulsating vacuum device to transmit rhythmic suction-relaxation manipulative action through tubing to applicators in contact with the facial and neck tissue."

In PCT international application No. PCT/FR95/00890, Guitay discloses a "massaging apparatus intending to perform massage treatments through an action of suction and mobilization of the skin tissue. It is comprised of parallel rollers . . . mounted inside a casing . . . and between which is created a depression when the apparatus is applied against the patient's body."

In U.S. Pat. No. 5,665,053, Jacobs discloses "an endermology body massager having at least two rollers spaced from each other in a parallel configuration. The rollers rotate in the same direction and are rotatably mounted movable axes. A vacuum source is connected to the chamber that houses the rollers."

U.S. Pat. No. 5,215,078 to Fulop discloses "a massager [which] includes an electric motor driven eccentric cam . . . in a housing . . . A moving member . . . is slidably mounted on the housing and is driven by the eccentric cam in a reciprocating, translatory motion relative to the housing."

Using a roller as a lifting or petrissage element in a body contouring or massage device as disclosed in some of the prior art above can be disadvantageous in that use of rollers increases the manufacturing cost of the device and complicates assembly of the device. Cost and complexity of manufacturing are especially increased for devices employing rollers which are motorized or otherwise mechanically activated. Similarly, maintenance and repair of devices with rollers can increase the overall cost to the purchaser. Devices with moving parts may require regular replacement of the moving parts which malfunction or wear out. Moreover, motorized and mechanized roller devices can be difficult to clean and may require partial disassembly to clean. Some rollers also limit the direction and movement of the device along the skin of the patient, restricting movement of the device to substantially forward and backward movements. In this way, roller devices limit the types of treatments that can be offered using the device and may prove difficult to use.

It has been found that there is discomfort related to prior art designs of massage and body contouring devices. For example, in devices using rollers, the patient's skin may be pinched. As the roller moves along the surface of the skin, the skin can be drawn up along the roller and get caught in the space between the roller and the housing of the device.

Where the lifting action of the skin is increased by motorized or mechanically activated rollers or by a vacuum source, the patient's discomfort from pinching may increase. The design of the housing of the device may increase a patient's chances of uncomfortable contact with sharp edges or corners of the housing, such as with a square or angular shaped device. In devices using vacuum suction to lift the skin, if the portion of the device which contacts the patient's skin to create the vacuum seal has sharp edges, the vacuum suction may cause the skin to be pinched along the area of the seal. This is particularly the case when the vacuum suction becomes too strong, and there is no safety release valve to reduce the suction. A patient's skin may also be irritated by the device where the device comes into direct contact with the skin.

Microdermabrasion techniques and systems are also well known to those skilled in the art. A typical dermabrasion system includes a pneumatic drive, such as either a negative pressure system or a positive pressure system, that delivers an ablative material from a supply point to a hand piece, also known as a wand, which has a small aperture to be placed upon a patient's skin during the abrasion process. In the negative pressure system, such as one utilizing a vacuum for pneumatic drive, the closing of the aperture by the skin completes the pneumatic circuit drawing the abrasive material to the skin to perform dermabrasion. The refuse and debris after the abrasive procedure is vacuumed away into a waste storage container for disposal.

Each stage of operation within current dermabrasion systems suffer problems that prevent optimal and efficient operation on a subject or patient. One problem is the handling of the abrasive material at the supply point. Typical supply points utilize abrasive supply containers that are permanently mounted and must be refilled when empty. These containers are usually difficult to access and lead to waste and unnecessary exposure to the abrasive material during filling. Further, due to the dynamics of the content level changing, the systems fail to deliver consistent amounts of abrasive material from the supply containers to the hand piece. As such, the results of the abrasive operation are inconsistent and vary in the length of time normally needed to perform a typical procedure/session. As the container goes from full to empty, performance can suffer severely, with as much as a 75 percent reduction in abrasive concentration in the air stream. Additionally, few, if any, systems are able to utilize all the contents of the supply container before needing refilling.

An additional problem with current supply containers is that they draw upon ambient air. Ambient air is often humid and the moisture therein causes the moisture-sensitive abrasive to agglomerate and subsequently clog the system. This is especially a problem in that most systems utilize a small output aperture that clogs easily, particularly when the abrasive material becomes damp with humidity, leading to clumping and clogging and generally inconsistent delivery of abrasive. Often, the existing systems are induced to employ mechanical or pneumatic means, such as spring-loaded rods or compressed air, to periodically clear the restricted output aperture.

Another part of the abrasive delivery system is an abrasive/concentration control system. Most systems lack such a control system. The control system's purpose is to control the amount of abrasive delivered to the hand piece during operation. Some systems utilize an electronic control that causes pulses resulting in pressure surges and non-uniform delivery of the abrasive. Other systems utilize control systems that are difficult to adjust, hard to reset and fail to provide repeatable consistent results for subsequent treatments.

The hand piece is a critical component of any dermabrasion system. Hand pieces suffer several problems. One problem is that the apertures tend to restrict the flow of the abrasive material to the skin as well as hinder removal of the abraded material and the abrasive during the abrasion procedure. Further, the dermabrasion procedure involves removal of skin and sometimes blood, so there is concern that the use of the same wand from patient to patient is unsanitary and unhealthy. Attempts to make the hand piece more hygienic by having disposable and replaceable wand tips has been unsuccessful as the tips merely prevent contamination at the aperture level without addressing a problem known as back contamination, which occurs when refuse debris within the wand from a previous procedure contaminates the wand tip in spite of the replacement of a fresh tip.

Further, some hand pieces are designed without thought about how the hand piece is to be cleaned. As such, these pieces are difficult to clean and therefore, undesirable for long term use. Also, most hand pieces are expensive to manufacture. They can be heavy and awkward to use, such that the technician suffers discomfort and fatigue during long sessions or over several sessions during the same day. Since the piece needs to be small enough to handle, they often have restricted flow paths that detrimentally affect flow rate and delivery of the abrasive for optimal results and for quick pick up of the waste debris.

Another element of the dermabrasion system includes a waste recovery or accumulation container system. Most systems are permanently mounted and are difficult to access, empty, and clean. The containers collect abrasive dust along with skin cells, and bodily fluids, which may contain microbes or other undesirable elements. As such, the containers must be emptied and cleaned periodically. Failure to clean the container can result in unwanted growths and other hazardous health risks that should be avoided at all times.

The waste accumulation systems often have small exhaust apertures that can easily clog with waste products resulting in restricted air flow within the overall system. Moreover, filter elements are also employed to prevent abrasive and debris out flow into the vacuum source. Such filters are a major source of clogging and reduction of optimal air flow within the entire system, thereby leading to poor dermabrasion results since less abrasive material is being carried within the system at a reduced speed. Similar to the supply system, one solution has been to use back pressure to clear and clean the filters or unplug the clogs in the waste accumulation system, but this adds cost and complexity to the overall design, which can result in mechanical failure, decreased abrasion performance, and increased costs of production and operation.

Accordingly, what is needed is a dermabrasion system and method that overcomes the problems of the prior art. Specifically, what is needed is a dermabrasion system that controls the dispersion of the abrasive material over the entire range of operation uniformly and consistently over the prior art methods. Further, what is needed is a method and system for handling the abrasive material prior to the ablative operation and afterwards during the collection of the contaminated materials. Further still, what is needed is a hand piece that is lightweight and easily cleaned to meet high health safety standards, yet allows for high air flow.

SUMMARY OF THE INVENTION

It is reported that the size of fat cells in superficial adipose layers can be affected through external massage. Specifically it is reported that vasodilation in combination with physical force upon a fat cell can remove volume from the fat cell into lymphatic and venous channels, creating a chance to eliminate this volume from the body through the kidneys or to bum it by exercise. The present invention may provide a mechanical means for creating an environment into which the volume of fat cells and superficial adipose layers may be reduced using positive and negative pressure on the skin above the superficial adipose layer.

The present invention provides a means for applying positive and negative pressure on the skin. More specifically, the present invention provides a means for applying positive pressure on an area of skin undergoing negative pressure. As used herein, the term "skin" refers primarily to the epidermis and dermia but may include other deeper dermal and non-dermal tissues and associated structures. The device also includes a kneading, or petrissage element and a stroking or effleurage element.

Generally, the device comprises a head, a post and a handle. The head being substantially spherical or semi-spherical and defining a broad, substantially flat rim and a concave cavity with an opening.

Extending from the wall of the concave cavity toward the opening is a post. The post is connected to the head but a portion of the post is free. The free portion of the post extends toward the rim and may be slightly recessed within the cavity. The free portion provides a skin contact surface. The post may be substantially cylindrical, the cylindrical post being connected to the head at one end of the cylinder and having a skin contact surface on the other end. The contact surface can be substantially flat and/or fixed, a fixed contact surface being one that does not move relative to the post or head. The rim, as defined by the head, also has a contact surface which can be substantially flat and/or fixed. The head defines an orifice leading from the cavity to the vacuum source.

The handle is connected to the head at one end of the handle. The handle defines an internal conduit running lengthwise inside the handle, the conduit having two open ends. On one open end of the conduit, the conduit opens into the orifice defined by the head; the second open end of the conduit is connected to the vacuum source.

The head includes an outer or peripheral effleurage element and the post includes an inner or central effleurage element, the outer element being externally and radially outward from the internal effleurage element.

The vacuum source has a bleed-off valve in order to avoid subjecting a patient to excessive vacuum pressure. A barrier between the skin and the device is used to reduce or prevent possible irritation from contact of the device with a patient's skin and to allow the device to move more freely along the skin.

Also according to the present invention, a method and system for performing abrasion on a surface, such as on the skin of a patient, are disclosed. The dermabrasion apparatus includes means for delivering and retrieving material to and from a selected site to be abraded, a delivery and retrieval hand piece, an abrasive handling device, and a waste retrieval holding device. The hand piece is coupled to the abrasive handling device as well as the waste retrieval holding device, which is further coupled to the delivery and retrieval means. The abrasive handling device further includes an abrasive supply device, a receiving channel, a feeding chamber, and a delivery channel. The abrasive supply device typically is a canister fitted with a funnel-shaped spout that is inverted into the receiving channel. The receiving channel feeds abrasive to the feeding chamber. The delivery and retrieval means, typically a vacuum source that generates a pneumatic air supply within the abrasion apparatus, causes the abrasive within the feeding chamber to loft in an arc such that it reaches the delivery channel. The abrasive travels through the delivery channel under pressure to the hand piece, which is utilized to apply the abrasive to the surface and then retrieve the waste debris from the procedure. The abrasion apparatus may also include a massage or body contouring system, which also utilizes the vacuum source.

Further, the receiving channel extends within the feeding chamber and serves to limit or control the amount of abrasive filling the feeding chamber. The receiving chamber's height, relative to its location within the feeding chamber, can be adjusted by way of an height adjustment means. The feeding chamber typically comprises top and bottom portions as well as generally sloped side walls that slope inwardly from the top to the bottom. Such geometries lend themselves to the shapes including funnels, inverted pyramids, bowl shapes, and other geometries where the walls are sloped in such a fashion so that the abrasives accumulate in a concentrated point at the bottom. Placed between the supply device and the feeding channel is an additional chamber that provides for the abrasive to feed within the receiving channel without blocking the insertion of the funnel within the supply device. The feeding chamber is further coupled to an ambient air supply with a filter interspersed between ambient and the feeding chamber to prevent unwanted matter from being drawn within the apparatus as well as to prevent abrasive from spilling out an open aperture where the ambient port is located.

The dermabrasion hand piece comprises a body having a first end, a second end, a delivery channel, and a retrieval channel. The delivery channel extends the length of the body and the retrieval channel is concentric with the delivery channel, but has a larger diameter. A delivery aperture is located at the first end of the body. A retrieval aperture is placed adjacent and generally concentric with the delivery aperture. The delivery aperture is coupled to the delivery channel while the retrieval aperture is coupled to the retrieval channel. The dermabrasion hand piece further includes a dermabrasion tip that has a first end, which is removably mounted to the first end of the body, a second end, and a delivery aperture in the second end. The delivery aperture is generally concentric with the delivery channel and the delivery aperture. The tip is generally dome shaped and is made from a high density plastic or metal to withstand the abrading effects of the abrasive during operation. At the second end of the body are located an intake aperture and an outlet aperture. The intake aperture is concentric with the delivery channel while the outlet aperture is connected to the retrieval channel and is offset from the intake aperture.

The body may be further comprised of two portions, a body section and an end portion. Inserted between the end portion and the body portion is a hollow tube, which serves as the delivery channel. Further included in the hand piece is a nozzle that is placed at the first end of the body adjacent the delivery aperture. The nozzle has an opening for concentrating the abrasive as it passes through the nozzle. Further included is an optional nose tube, which is concentric with the delivery channel and the nozzle, and is placed adjacent the nozzle at the first end of the body. The tip mounts to the first end of the body and an anti-bleed seal is provided by an o-ring mounted on the first end of the body and engages with an inner-perimeter of the first end of the tip.

The waste debris collection device includes a waste can receiver, a waste canister, and a filter. The waste canister includes an intake port and return port. The intake port is coupled to the hand piece and the return port exits to ambient and includes a filter to prevent waste debris from being discharged to ambient. The waste canister typically is the same type of canister that is used initially to feed the abrasive to the feed chamber. The waste canister removably couples to the waste can receiver and a filter is fitted between the waste can receiver and the waste canister. The filter has a center intake port aperture in which the intake port passes, but the return path of the air drawn by vacuum passes through the filter, thus trapping the waste debris within the waste canister. A filter frame is used to support and retain the filter in position between the waste can receiver and the waste canister where the filter has substantially the same area as the opening of the waste canister. Pliable retention rings are used to secure the filter in place between the waste canister and the filter frame support.

In yet another embodiment of the present invention, a combined massage and dermabrasion unit are described that utilize the massage system as well as the dermabrasion system of above in a convenient to use system that utilize a common vacuum supply. Both the massage system and the dermabrasion system may be used in the same treatment session. The use of both systems in the same treatment session leads to a more rapid healing and rejuvenation of a patient's skin surface as the massage action encourages blood flow to the skin surface.

BRIEF DESCRIPTION OF THE DRAWINGS

The foregoing and other features of the present invention will become more fully apparent from the following description and appended claims, taken in conjunction with the accompanying drawings. Understanding that these drawings depict only typical embodiments of the invention and are, therefore, not to be considered limiting of its scope, the invention will be described with additional specificity and detail through use of the accompanying drawings in which:

FIG. 2 shows the embodiment of FIG. 1 in longitudinal cross section;

FIG. 3 shows one embodiment of the present invention having a post capable of being releasably secured to the head;

DETAILED DESCRIPTION OF SPECIFIC EMBODIMENTS

It will be readily understood that the components of the present invention, as generally described and illustrated in the Figures herein, could be arranged and designed in a wide variety of different configurations. Thus, the following more detailed description of the embodiments of the apparatus and methods of the present invention, as represented in FIGS. 1 through 12, is not intended to limit the scope of the invention, as claimed, but it is merely representative of specific embodiments of the invention.

The specific embodiments of the invention will be best understood by reference to the drawings, wherein like parts are designated by like numerals throughout.

The present invention comprises a device and method for applying positive pressure to an area of skin undergoing negative pressure. Subjecting an area of skin to negative pressure allows blood and lymph vessels beneath the area of skin being treated to dilate. Positive pressure applied to a portion of the skin area undergoing negative pressure causes vessels to be constricted. In combination, the positive pressure applied to an area of skin undergoing negative pressure results in increasing the supply of oxygen and nutrients to the skin, increasing venous and lymphatic drainage, and potentially disrupting fat cell membranes.

Figure 1:
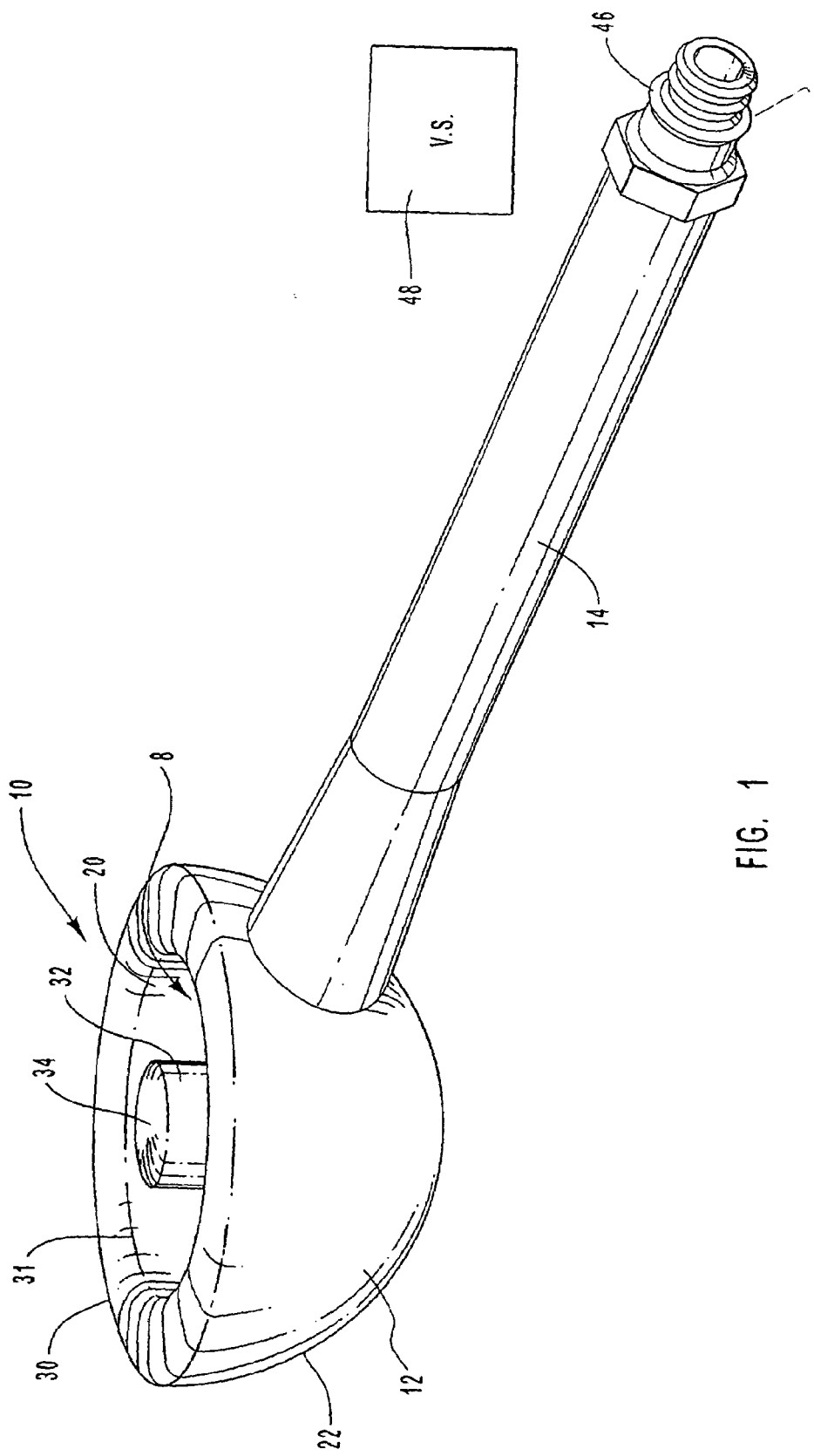
FIG. 1 shows a perspective view of one embodiment of the present invention.

The device 10, shown in FIG. 1, comprises a means for applying negative pressure to an area of skin and means for applying positive pressure to the area of skin undergoing negative pressure. As explained above, negative pressure is a lifting of the skin or a reducing of pressure above and around an area of skin. The raising or lifting of the skin may be effected by bringing the skin into contact with an adhesive surface or applying a force to the skin along a vector which raises the skin, or reducing the atmospheric pressure above the skin by creating a vacuum to atmosphere above the surface of the skin. Alternatively any means by which skin may be safely raised above its resting position can be used to create negative pressure.

In one embodiment, means for applying negative pressure to an area of skin is accomplished by creating negative pressure within cavity 8. Means for applying negative pressure to an area of skin comprises a head 12 defining a cavity 8. Head 12 is substantially semi-spherical, although it will be readily appreciated that other shapes may be used for head 12 consistent with the present invention. Cavity 8 is defined by a substantially concave inner wall 24 of head 12, as shown in FIG. 2. Head 12 has a substantially convex outer wall 22. Head 12 also defines a rim 30. Rim 30 defines an opening 20 which leads to cavity 8. At least one orifice 26 is defined by inner wall 24. Orifice 26 communicates with a vacuum source 48, such as by means of a hose 72 (see FIG. 7). Vacuum source 48 creates a vacuum to atmosphere within cavity 8.

Means for applying positive pressure is also provided by device 10. Positive pressure, briefly described above, is a compression of or increase in the pressure on an area of skin. Positive pressure may be affected by directing a force along a vector which physically compresses the skin. The positive pressure may be provided by physical contact between the device and the skin. Likewise, increasing air pressure around a portion or area of skin can provide positive pressure.

More specifically, means for applying positive pressure to an area of skin undergoing negative pressure comprises a post 32. As depicted in the Figures herein, post 32 is substantially cylindrical in shape and has a substantially flat contact surface 34. However, post 32 may also have other shapes consistent with the present invention. Post 32 has a diameter 36 and a length 38. The length 38 is such that post 32 is slightly recessed within the cavity 8 defined by head 12 and rim 30. Post 32 is connected to head 12 and extends away from concave inner wall 24, connecting to the head 12 at approximately the apex or center 28 of the concave inner wall 24, as shown in FIG. 2. It is contemplated that post 32 could be connected to concave wall 24 at points other than center 28. In the disclosed embodiment, a single post 32 extends from concave wall 24, however a device having more than one post 32 is also contemplated. In one embodiment, the post may be fixed but it is contemplated that the post may be movable such as up and down along its longitudinal axis or from side to side in pendulum fashion, when in use.

Handle 14 is connected to head 12 at one end and has an internal conduit 44 running longitudinally inside handle 14. The conduit inside handle 14 has a first open end and second open end. The first open end communicates with orifice 26. The second open end has means for attachment to a vacuum source 48. Handle 14 is preferably substantially cylindrical, having a length greater than its diameter and a circumference suitable for grasping by the user's hand. The surface of handle 14 may be grooved or otherwise have an ergonomic design. A vacuum source attachment means may be a vacuum hose adapter 46 or any suitable means of connecting conduit 44 to vacuum source 48.

Alternatively, handle 14 may be solid and orifice 26 may be connected to vacuum source 48 through a conduit 44 located outside handle 14. For example, conduit 44 may be a tube or conduit 44 communicating at a first open end of the tube with the vacuum source 48 and communicating at a second open end of the tube with orifice 26.

Using the device, an area of skin can be brought under negative pressure by bringing rim 30 into contact with the skin, sealing off opening 20 and creating a substantially air-tight seal between the skin and the rim 30. Rim 30 has a broad, substantially flat contact surface 31 allowing a broad seal with the skin. Negative pressure on the skin occurs as vacuum source 48 creates a pressure differential within the cavity 8. A substantially semi-spherical concave inner wall 24, assists in creating a generally uniform area of negative pressure. The absence of edges and corners along the concave inner wall 24 helps reduce uncomfortable contact between the skin and inner wall 24 and provides for a better seal with the skin. The broad, substantially flat contact surface 31 of rim 30 and the relatively long radii of curvature of the rounded edges along rim 30, as shown in FIGS. 1–4, prevent the negative pressure from lifting and pulling uncomfortably on the skin, and particularly the skin which by its contact with the rim, creates the seal at the perimeter of the area under pressure. An area of skin is lifted by the pressure differential in cavity 8 (negative pressure) when the skin and rim 30 of head 12 come into contact to form a substantially air tight seal.

Generally, the device 10 is designed to have few edges. Specifically, rim 30 is designed to be substantially circular with rounded edges on either side of the broad, substantially flat contact surface. Similarly, post 32 is designed to be substantially circular with rounded edges adjoining the broad, substantially flat contact surface. A relatively long radius of curvature used in rounding edges increases the comfort to both patient and user and prevents uncomfortable contact with the device.

The device is functional with a post 32 that is not recessed within cavity 8, however, it is preferable that the post be recessed within cavity 8 creating a better seal between rim 30 and the surface of the skin. The improved seal allows for use of the vacuum at lower vacuum levels while maintaining an appropriate level of negative pressure within cavity 8.

Post 32 and rim 30 provide a positive pressure to the skin. Positive pressure to the area of skin undergoing negative pressure is achieved by post 32. Post 32 resists the negative pressure or lifting of the skin and places positive pressure on a portion of the skin undergoing negative pressure. Post 32 contacts skin which is inside the perimeter of the area undergoing negative pressure. Thus, when the device is in use and rim 30 creates a seal with the skin and thereby defines an area under negative pressure, rim 30 applies positive pressure the skin along the perimeter of the area under negative pressure and post 32 also applies positive pressure, the pressure from post 32 being, radially interior to the perimeter of the area under pressure. Negative pressure within the cavity 8 provides a creasing or lifting of the skin.

More than one post 32 is contemplated to be incorporated in the massage unit. Specifically, two or more posts can be provided in alternative embodiments to enhance the negative pressure desired in the present invention.

With negative and positive pressure applied to the skin, the device can be moved along the surface of the skin. The free movement of head 12 along, the skin is greatly enhanced by its substantially semi-spherical shape and by post 32. Rim 30 is substantially circular, and post 32 is substantially cylindrical allowing the device to be easily moved in any direction along the surface of the skin, without having to break contact with the skin or re-orient the device. For example, post 32 facilitates movement of the device by limiting the height to which skin is lifted in cavity 8, thereby limiting the resistance to movement that could otherwise result from the lifted skin and allowing the device to move without the use of rollers. In other words, the device 10 is not limited to generally back and forth movements, as are cylindrical roller devices, and device 10 can be moved along the surface of the skin in any number of directions and patterns. As illustrated graphically in FIG. 5, device 10 can be comfortably moved in spiraling (FIG. 5A), wave (FIG. 5B), circular as well as other patterns along the skin.

Figure 6:
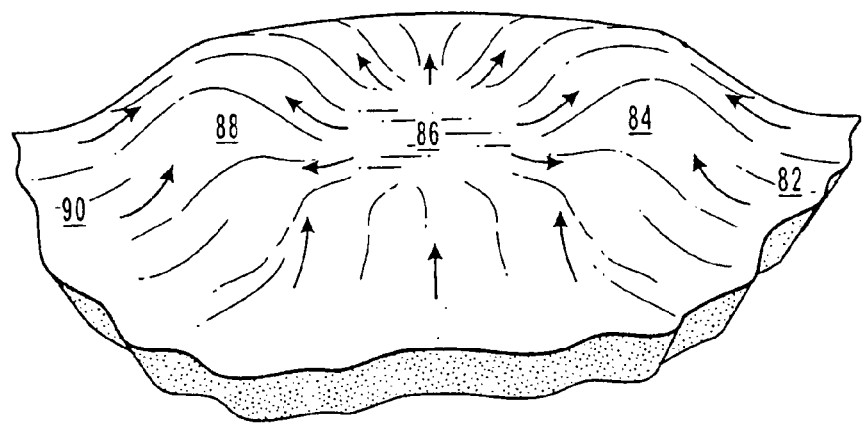
FIG. 6 illustrates positive pressure on an area of skin undergoing negative pressure.

The positioning of post 32 radially interior to rim 30, with space between post 32 and rim 30 allows for an intermittent positive pressure and negative pressure effect on an area of skin as the head is moved along the surface of the skin. Referring to FIG. 6, as head 12 passes over a given area of skin, rim 30 provides initial positive pressure to the skin at 82. As the head is moved, the area of skin is next exposed to negative pressure within cavity 8, as shown at 84. As the head is moved still further, post 32 passes over a portion of the area of skin, as depicted at 86, producing positive pressure within the negative pressure area. The skin is then released from beneath the positive pressure of post 32 into the negative pressure of cavity 8 a second time, as illustrated at 88, and thereafter undergoes a final positive pressure from rim 30, as depicted at 90.

Rim 30 has a broad, substantially flat contact surface 31 which provides a stroking or effleurage-like massaging technique as the device passes over the skin, as does the substantially flat, contact surface 34 of post 32. Negative pressure created in cavity 8 lifts the skin. Both the inner wall 24 and the edge of rim 30 in combination with post 32 knead the lifted skin as the device is moved along the skin. This provides a petrissage-like massage technique as the device passes over the skin.

The radially interior positioning of post 32 relative to rim 30 also provides for intermittent effleurage-and-petrissage type massaging. The substantially flat contact surface 31 of rim 32 provides initial effleurage-like or stroking massage as it passes over an area of skin. The area of skin is then lifted as it is exposed to the negative pressure in cavity 8. Post 32 kneads the lifted area of skin. The substantially flat contact surface 34 of post 32 then passes over a portion of the area of the skin giving the stroking, effleurage-like massage. The skin is released from beneath post 32 into cavity 8, where the skin is lifted and kneaded by the edge of rim 30 and inner wall 24 of cavity 8. Finally, the substantially flat contact surface 31 of rim 32 then provides a stroking, effleurage-like massage.

The positive pressure provided by both post 32 and rim 30 in combination with the negative pressure created within cavity 8 creates a unique and effective area of positive and negative pressure along the portion of skin immediately surrounding and beneath post 32. As explained above, post 32 provides a positive pressure which resists the negative pressure or lifting of the skin created by the suction in cavity 8. The cylindrical shape of post 32 within the semi-spherical cavity 8 allows the negative pressure within the cavity to pull or lift the skin beneath post 32 in multiple directions. In other words, skin located beneath post 32 is pulled in opposite directions by the suction created on all sides of cylindrical post 32 as shown in FIG. 6. Arrows in FIG. 6 indicate the direction of the pull on the skin due to suction from the vacuum source. It is believed that this multi-directional pull on the skin beneath the post increases the potential for disruption of fat cells within the superficial adipose layer and further enhances the contrasting positive and negative pressure effect on the skin.

In the disclosed embodiment, handle 14, head 12 and post 32 are a single unit, or in other words a single piece. The head piece is preferably manufactured of delron, though other plastics or materials could be used alternatively or in combination with delron. It is preferable that the device be made of a material that can be milled such as aluminum, brass, copper, steel, or other metals, or plastics, or similar materials or composites of such materials, so the device can be manufactured as a single unit, or in a single piece. Various sizes of the device can be constructed without changing the central features of the invention or complicating the invention by requiring redesign or miniature mechanization of elements of the invention. Milling also provides for a presently preferred finish.

In another embodiment, handle 14 and/or post 32 are releasably secured to head 12 as shown in FIG. 3, by means such as threads 27 and 33. A releasably securable post 32, allows the space between rim 30 and post 32 to be adjusted by using posts of different sizes to accommodate different levels of skin elasticity and increase patient comfort. Means for releasably securing the handle or means for releasably securing the post device include any securing means known in the art, for example, a threaded means, a slip-lock securing means, a pressure fitting means, hook and loop means, a fastener means or lashing means.

Figure 4:
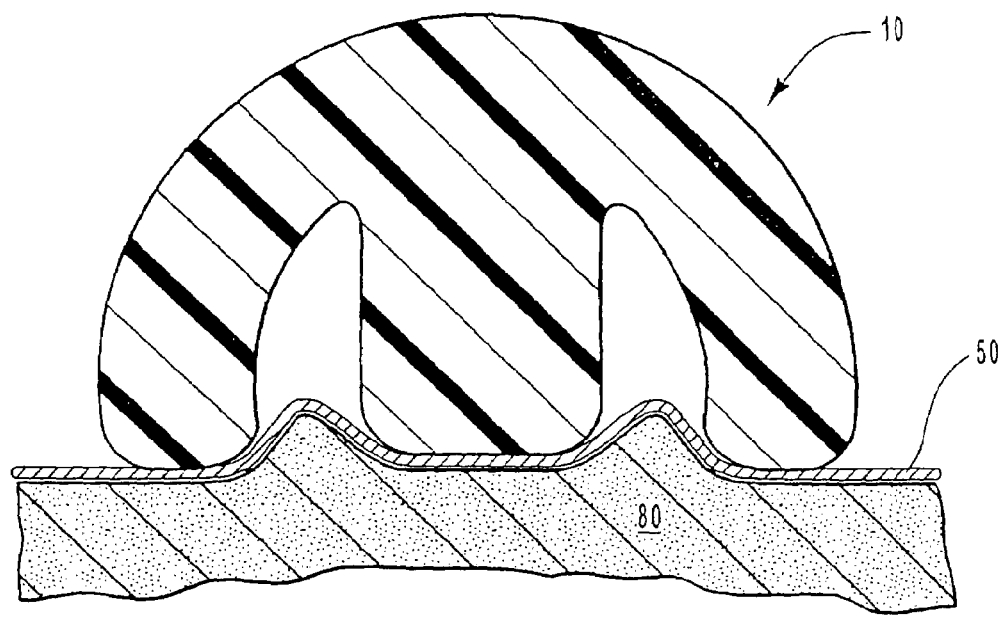
FIG. 4 shows use of the present invention with a skin barrier.
Figure 5A:
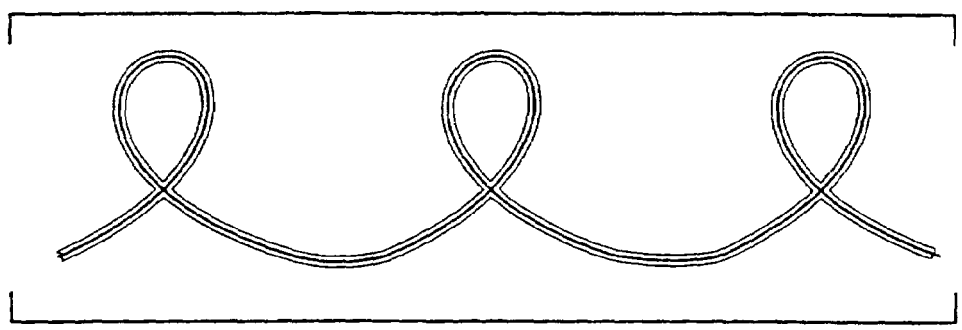
FIGS. 5A and 5B illustrates various methods of using the present invention.
Figure 5B:
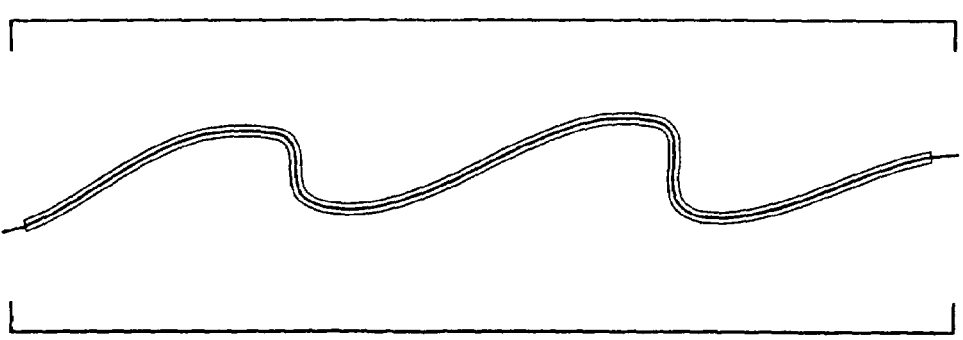

A barrier 50 shown in FIG. 4 can be placed on the skin 80 of the patient such that when the device is in use the barrier reduces or prevents possible irritation from direct contact between the skin 80 and the device 10. The barrier 50 can be solid or fluid. In one given embodiment, barrier 50 comprises a form fitting garment. Specific fluid or solid barriers 50, such as topical aminophylline gel, may enhance the therapeutic and/or cosmetic value of treatment with the device.

The use of heat in conjunction with the device is contemplated. The heat source can be external, such as heat packs and heat lamps, or the heat can be integral with the device. In the one embodiment the device 10 is heated prior to use.

A vacuum source 48 creates a negative pressure in cavity 8. Vacuum source 48 may be any suitable vacuum source known in the art. Vacuum source 48 is capable of varying the vacuum at discrete negative levels, such as 10 discrete pressure levels between 2 inches and 15 inches mercury. Vacuum source 48 is also capable of providing pulsating negative pressure levels, that is, increasing and decreasing pressure between two desired pressure levels, such as between any two negative pressure levels between 2 inches and 15 inches Hg. The pressure levels are selected according to patient comfort and desired treatment. In one embodiment, vacuum source 48 is an electric motor driven vacuum pump.

In one embodiment, the vacuum source is a microprocessor controlled vacuum pump such as a Gast ¾ horsepower high volume vacuum pump. The voltage requirements of the vacuum source are 120 volts, 60 hertz, 13 amps or alternatively 240 volts, 50 hertz, 9 amps. The vacuum source 48 communicates with the device 10 through a hose 72. In one embodiment, the hose dimensions are 1.27 cm by 244 cm, but may have alternative dimensions suitable to the device 10 and the vacuum source 48. The Gast vacuum pump has a maximum suction lift of 27 feet. The vacuum pump is calibrated to preset levels. Alternatively, the vacuum pump can be piston, rotary vane, diaphragm, linear, or any other vacuum pump technology known in the art.

Figure 7:
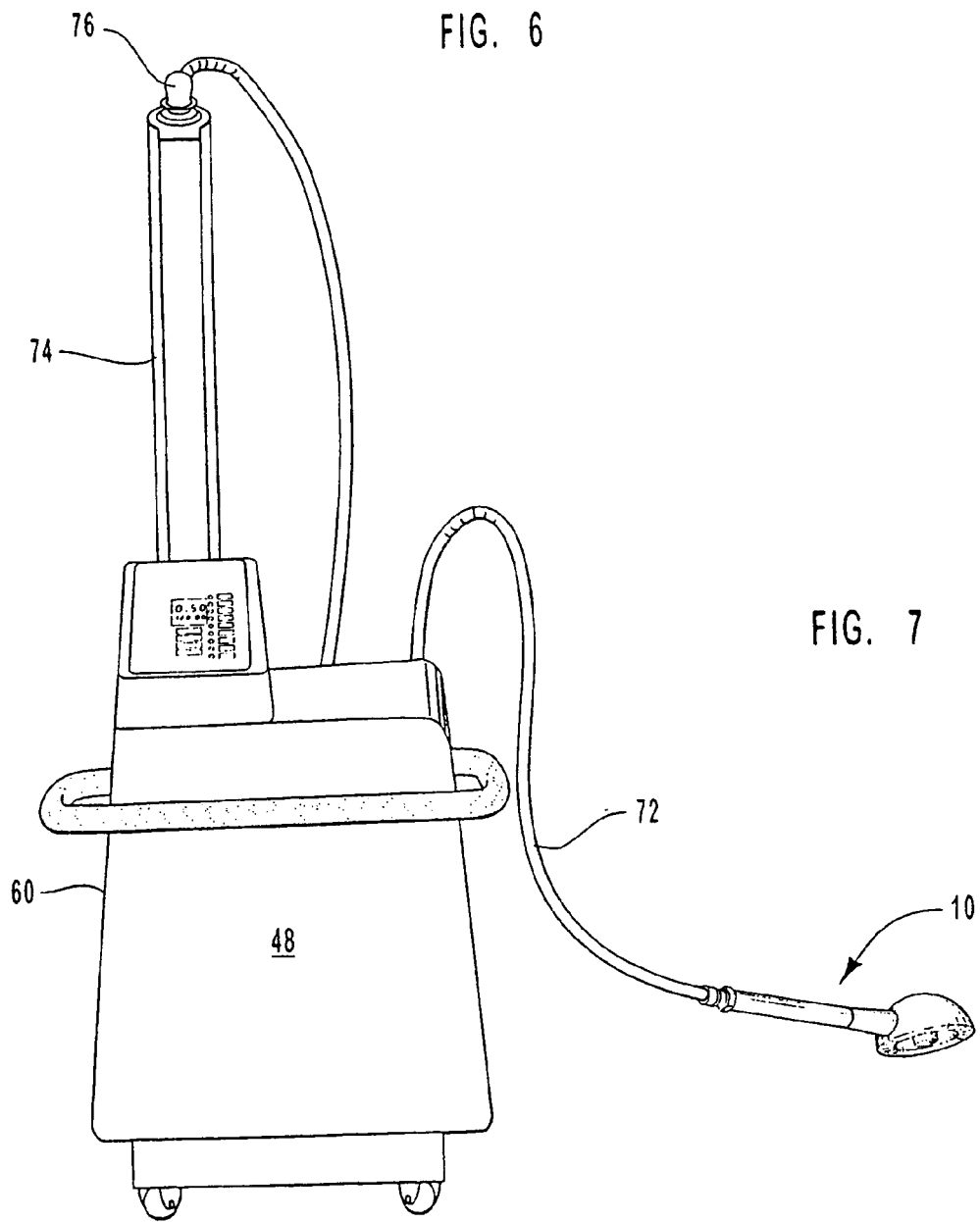
FIG. 7 shows a perspective view of the device attached to a vacuum source.

Vacuum source 48 may communicate with orifice 26 of device 10 by means of a tube 72 in combination with a boom 74 as shown in FIG. 7. Using a tube 72 in combination with a boom 74 helps to prevent unintended and potentially uncomfortable contact between the patient and the device and allows the user greater mobility.

A bleed-off valve 76 is connected to vacuum source 48 to limit the amount of negative pressure which can be brought upon the skin within cavity 8. The bleed-off valve 76 is disposed between handle 14 and vacuum source 48. In the presently disclosed embodiment, the bleed-off valve opens at a pressure of about 17 to 18 inches of mercury. The bleed-off valve allows for the release of excess suction in the system, thereby preventing uncomfortable and potentially harmful pressure differences from occurring in the system. In this embodiment, the bleed-off valve has an operating pressure range of 18 to 20 psi. Exhaust time is approximately 1 second. The valve is preferably composed of stainless steel, or similar metals. The valve is disposed between the vacuum source 48 and the device 10. In one embodiment, the bleed-off valve is located within the housing 60 of a vacuum source 48. Bleed-off valves suitable for the purposes described are known in the art and readily available. Festo, Inc. is a manufacturer of one specific bleed-off valve contemplated within the present invention.

Figure 8:
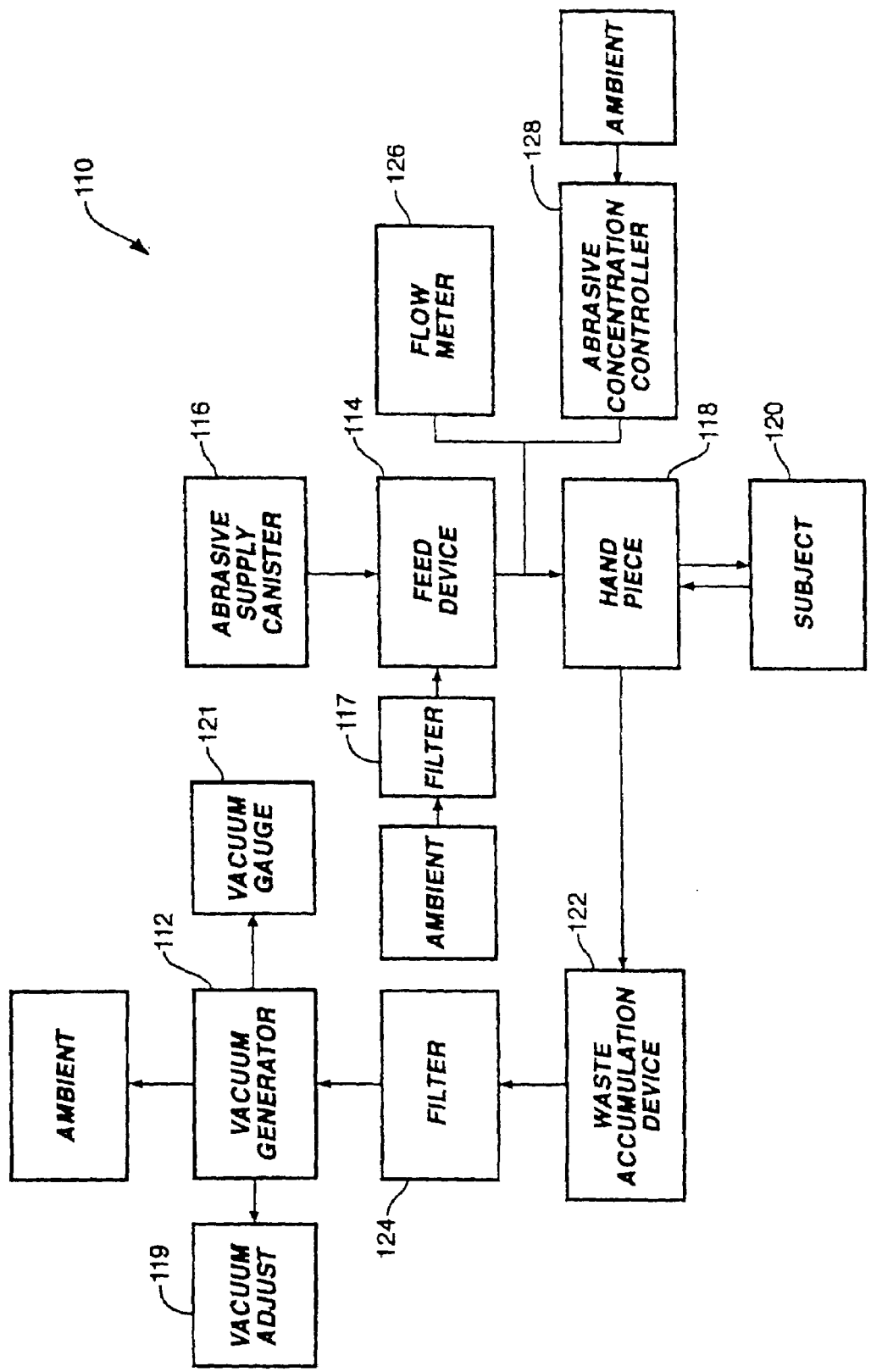
FIG. 8 depicts a schematic diagram of a dermabrasion system in accordance with the present invention.
Figure 9:
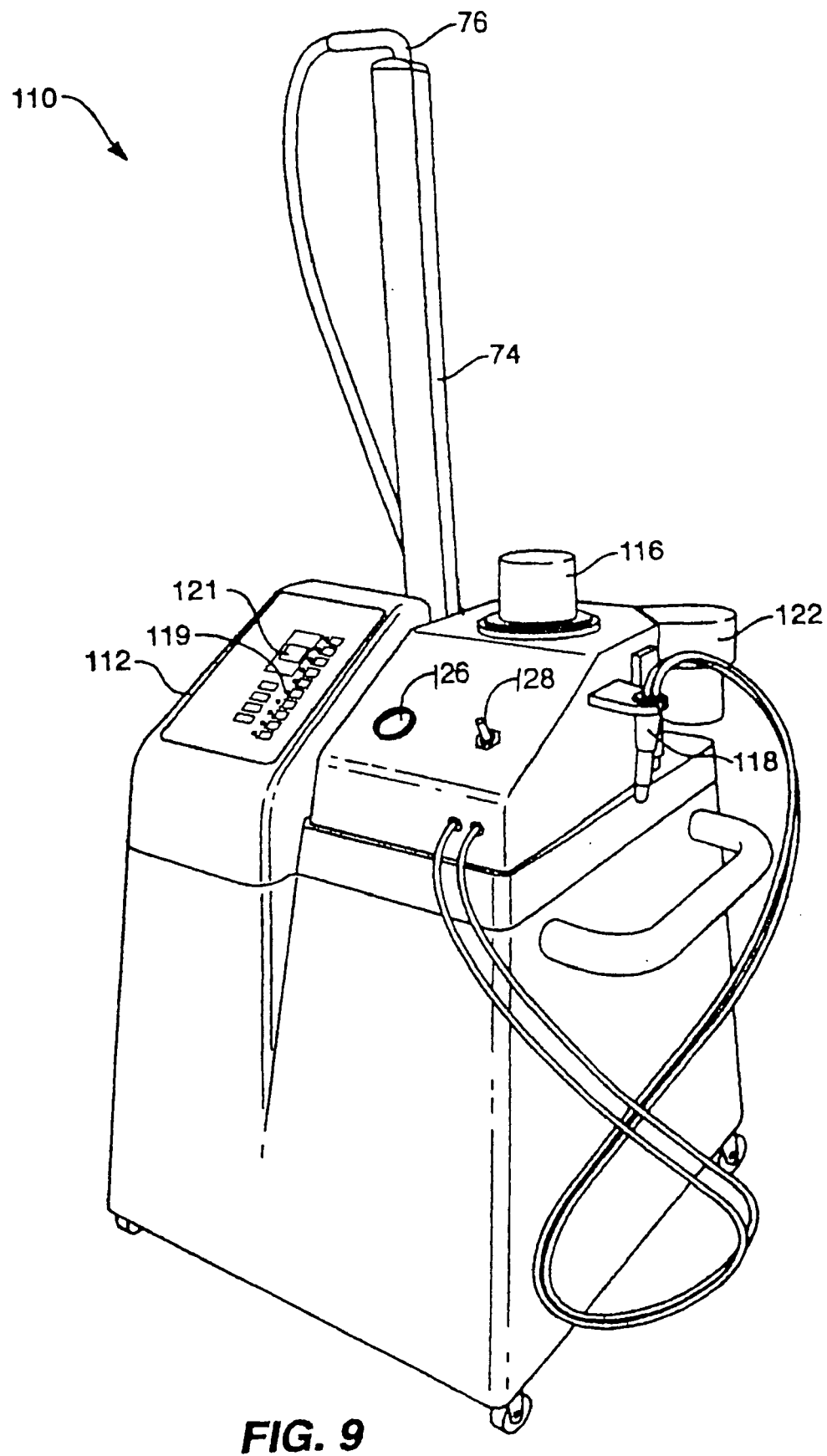
FIG. 9 illustrates a perspective view of the dermabrasion system in accordance with the present invention.

An abrasion system 110, which is optionally portable, is depicted in the block diagram of FIG. 8 as well as in FIG. 9. Dermabrasion apparatus 110 is a pneumatically driven apparatus that includes a vacuum generator 112. The pneumatic source may also be provided by a forced air system well known to those skilled in the art. Other pneumatic delivery systems will be readily apparent to those skilled in the art and should not be limited to solely a vacuum generator system or other forced air or compressed air delivery type arrangements. An airless pump may also be substituted as long as it provides adequate abrasive delivery and pick up though out the abrasion system.

Vacuum generator 112 also may be optionally coupled or decoupled from the remaining elements of the dermabrasion apparatus 110 and is not intended to be limited to only those dermabrasion systems that include self-contained pneumatic delivery systems. Further, since the dermabrasion apparatus 110 can utilize the vacuum generator 112 as disclosed in the cited patent application, it is possible to have both a dermabrasion apparatus and a massage or body contouring system.

Vacuum generator 112 couples to other elements within the system 110 via standard connection means. Vacuum generator 112 also vents to ambient during operation. A vacuum adjustment control 119 is provided with the generator to control the level of vacuum pressure generated thereby. The connection means can include metal or plastic tubing typically found in systems that are pneumatically operated.

The system 110 further includes an abrasive feed device 114 that couples to an abrasive supply canister 116 as well as to ambient. The ambient connection provides the needed air to deliver the abrasive from device 114 to the patient 120. A filter 117 is placed between the ambient source and feed device 114 to filter the incoming air supply as well as to prevent any abrasive within device 114 from exiting out the intake port from which ambient air is drawn. Both abrasive feed device 114 and abrasive supply canister 116 are shown in greater detail in FIG. 10. Filter 117 can be a sintered plastic, ceramic, or metallic filter that allows air to pass through, but not the abrasive. Other filters that can be utilized will be apparent to those skilled in the art such as membrane, fiber, and mesh filters, but are not limited solely to those named.

Abrasive feed device 114 further couples to a hand piece or wand 118, which is utilized to perform the dermabrasion on a patient or subject 120. The hand piece 118 provides both delivery of the abrasive material to the subject as well as retrieval of waste debris and abrasive during operation. This excess debris and material is deposited in waste collection device 122, which is also coupled to hand piece 118. A filter 124, such as another sintered or other suitable filter, serves to prevent any previously untrapped waste debris and abrasive from contaminating vacuum generator 112 or being vented to ambient, and is coupled between the waste collection canister 122 and vacuum generator 112. Waste collection or accumulation device 122 includes a filter (shown in FIG. 11B) that is used to prevent the vast majority of waste debris and abrasive from reaching filter 124 or vacuum generator 112.

Apparatus 110 includes a flow meter 126 and an abrasive concentration controller 128. Flow meter 126 displays the airflow generated within apparatus 110 so that the technician operating apparatus 110 can determine whether the airflow is sufficient for the procedure. Furthermore, flow meter 126 can also be used as a diagnostic device to determine if air flow within the system has fallen below acceptable levels due to clogging or fouling of filters. Should the technician need to adjust the airflow, the technician utilizes the vacuum level controller 119, which in this case is shown mounted on the control face of external vacuum generator 112.

Additionally, it may be desirable to vary the amount of abrasive in the air stream depending upon the nature of the procedure being performed. Toward this, the operator utilizes abrasive concentration controller 128 to mix ambient air into the abrasive-laden air coming from feed device 114 and leading toward hand piece 118. Flow meter 126 is well known to those skilled in the art and may be placed anywhere within the system where clean air flow occurs, i.e. before feed device 114 or after filter 124. In this example, the flow meter and concentration controller are both located proximate the hand piece.

Abrasive concentration controller 128 can be selected from a variety of controllers. For example, in one embodiment, the controller 128 is an infinitely adjustable rotary type that goes from full open to full close. It is the level of openness that determines the abrasive concentration in the system. Full open, which couples the hand piece to ambient and bleeds air into the system effectively reduces abrasive concentration to zero such that no abrasive is being delivered but that air flow and vacuum pressure remains unchanged. Such a situation is advantageous for removing used abrasive and debris from the patient's skin, as is often desired at the end of a treatment. Conversely, full close maximizes abrasive concentration. A multi-position toggle switch may also be utilized that selects between full open, full close, or one or more levels in between.

Further still, both flow meter 126 and abrasive concentration controller 128 can be either manually adjustable or electrically or electronically adjustable, depending upon the types of gauge sensor and pressure adjustment means selected and implemented. Electronic control provides for greater precision in abrasive delivery and treatment consistency between treatment sessions.

A vacuum gauge 121 and vacuum pressure adjustment means 119 are found on vacuum generator 112 within apparatus 110. Gauge 121 and adjustment means 119 are well known in the art.

Figure 10:
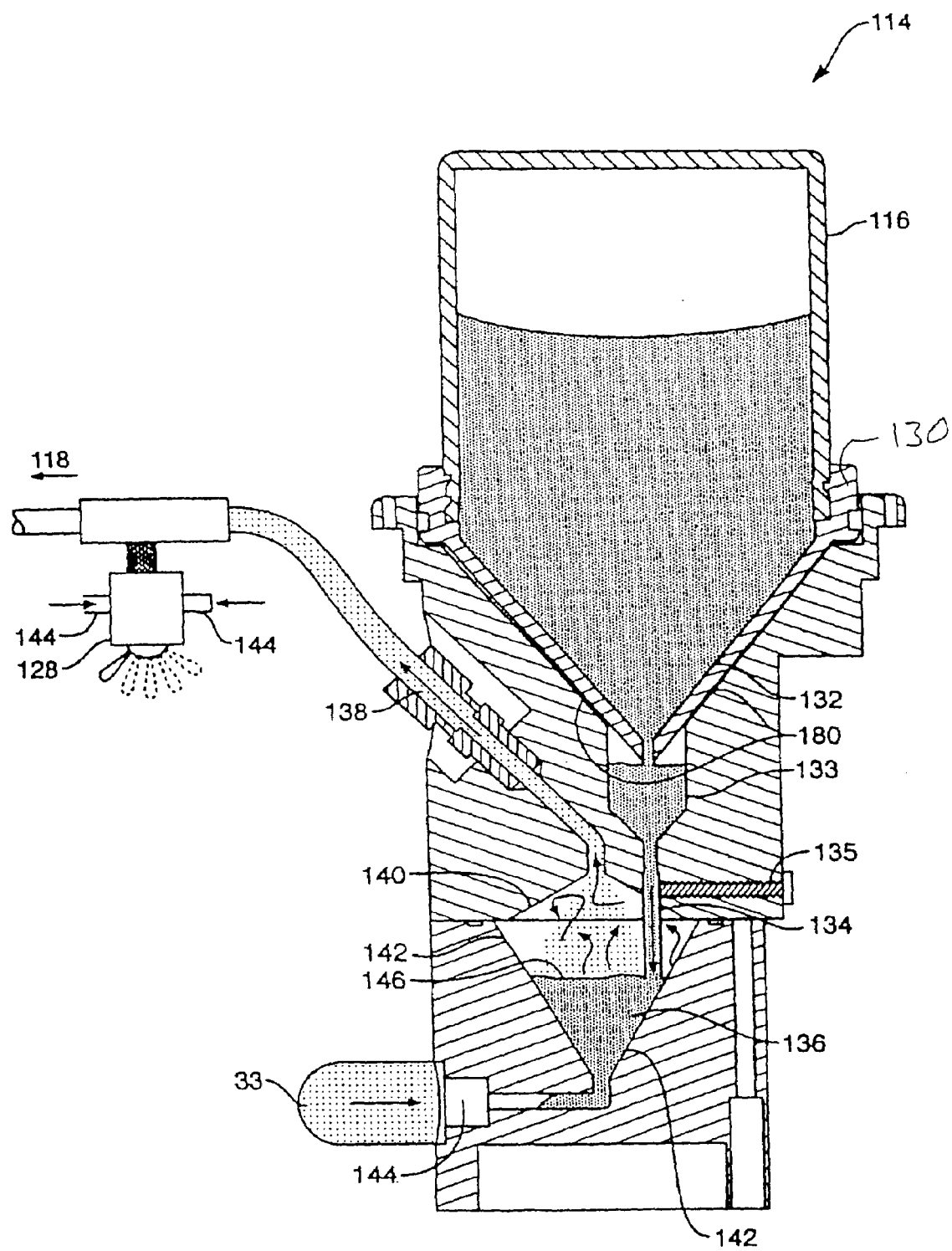
FIG. 10 illustrates the feeding device in accordance with principles of the present invention.

FIG. 10 illustrates the interaction of abrasive supply canister 116 with abrasive feeding device 114. Abrasive supply canister 116 further includes a funnel 130, which includes an aperture at the bottom tip to allow the abrasive stored therein to feed into abrasive feeding device 114. Abrasive supply canister 116 is typically a plastic or glass container having a threaded opening to which funnel 130 threads. A threaded cap (not shown) seals the canister 116 when it is does not have funnel 130 secured to it or when it is not mated to feed device 114, such as during transportation or storage. Abrasive supply canister 116 holds approximately one pound of abrasive material, but can hold more or less material in alternative embodiments. The abrasive material is selected from known particulate abrasives, such as aluminum oxide or other organic or inorganic micro-abrasive known to those skilled in the art.

Once the funnel 130 is placed on abrasive canister device 116, it is inverted so that the abrasive material is gravity fed within a holding chamber 132, which has a shape conforming to that of funnel 130. A transition chamber 133 is positioned between holding chamber 132 and feed tube 134. An arrow pointing downward shows the gravity feed direction of the abrasive material found in canister 116. The abrasive continues its gravity fall through feed tube 134, which has a defined length that extends within a feeding chamber 136. Further, feed tube 134 can be varied in length by control device 135 that raises or lowers tube 134 within chamber 136. This allows the operator to refine the abrasive flow within the system 110 by controlling the amount of abrasive that is allowed into chamber 136 during operation. Alternately, feed tube 134 can be of a predefined length which is fixed to the bottom of transition chamber 133 should adjustability not be required. Feed tube 134 can be substantially vertical or even angled to some degree so as not to interfere with the walls of feeding chamber 136. Optionally, the end of tube 134 is cut so as to be substantially horizontal in either configuration.

In alternative embodiments, feeding device 116 can include a vibrating motor that gently sifts the abrasive into feeding chamber 136. Further still, canister 116 can be mated to a feed tube that connects to tube 134 with the canister being suspended allowing the abrasive to gravity feed to chamber 136. The funnel 130 might then be mounted to a gimble mechanism or other rotational mechanism which would allow the canister to be mated to it in a substantially upright position and then rotated to an inverted position to thereupon allow gravity-feed of the abrasive via the connecting feed tube.

Feeding chamber 136 is illustrated to have a cone shape having an arc ranging from 40 degrees to 90 degrees, with 60 degrees being preferred. This is but one embodiment and other configurations are possible. For example, chamber 136 can have an inverted pyramid shape, a bowl shape, a cylindrical shape, or a combination of these geometries so long as the abrasive lofts sufficiently to provide uniform and consistent abrasive flow out of feeding chamber 136. Likewise, the shape of holding chamber 132 can be any of these types of geometries so long as the abrasive feeds to feeding chamber 136 uniformly and consistently without waste or clogging.

One end of feed tube 134 extends into lofting chamber 136. The bottom end of feed tube 134 limits the amount of abrasive that can be held within chamber 136. This limit is shown by line 146. It is by controlling of the amount of abrasive material within feeding chamber 136 that improves the delivery of a uniform and consistent supply of abrasive to hand wand 118 during operation. The abrasive material is lofted in the chamber during operation before exiting through transport tube 138. Transport tube 138 further couples to hand wand 118 for delivery of the abrasive material to the subject 120. In this embodiment, a vacuum is drawn on transport tube 138 with an ambient air source coming in through port 144. The ambient air passes through filter 133 into the bottom of feeding chamber 136. As the vacuum forms within feeding chamber 136, air is effectively bubbled through the abrasive pile and the abrasive particles are thereupon lofted and directed towards tube 138 via a feed funnel 140 formed in the top of feeding chamber 136. Feed funnel 140 has an arc of greater than 90 degrees with an aperture into tube 138. Funnel 40 serves to feed the lofted abrasive material through tube 138 to hand piece 118 during operation. The sloped side walls 142 of feeding chamber 136 serve to enhance the uniform delivery of abrasive material even while the contents of abrasive supply canister 116 empty completely into feeding chamber 136. The remaining arrows within feeding chamber 136 illustrate the physical action of the abrasive material during the operation of apparatus 110 as well as the final direction through tube 138 as the abrasive material is carried to hand piece 118.

An ambient port 144 is coupled between tube 138 and hand piece 118 and includes a variable open/close device that functions as controller 128 to control the amount of air bled into the abrasive stream during operation, thereby controlling the concentration of abrasive delivered to hand piece 118. In an alternative embodiment, the height of funnel 140 relative to feeding chamber 136 can be increased or decreased to change the abrasive feed characteristics according to the technician's preference.

Abrasive feeding device 114 is typically made from a durable material, such as aluminum, stainless steel, or high durability plastic material. Device 114 can also be made from other materials as long as they are inert to the abrasive and durable for operation.

Figure 11A:
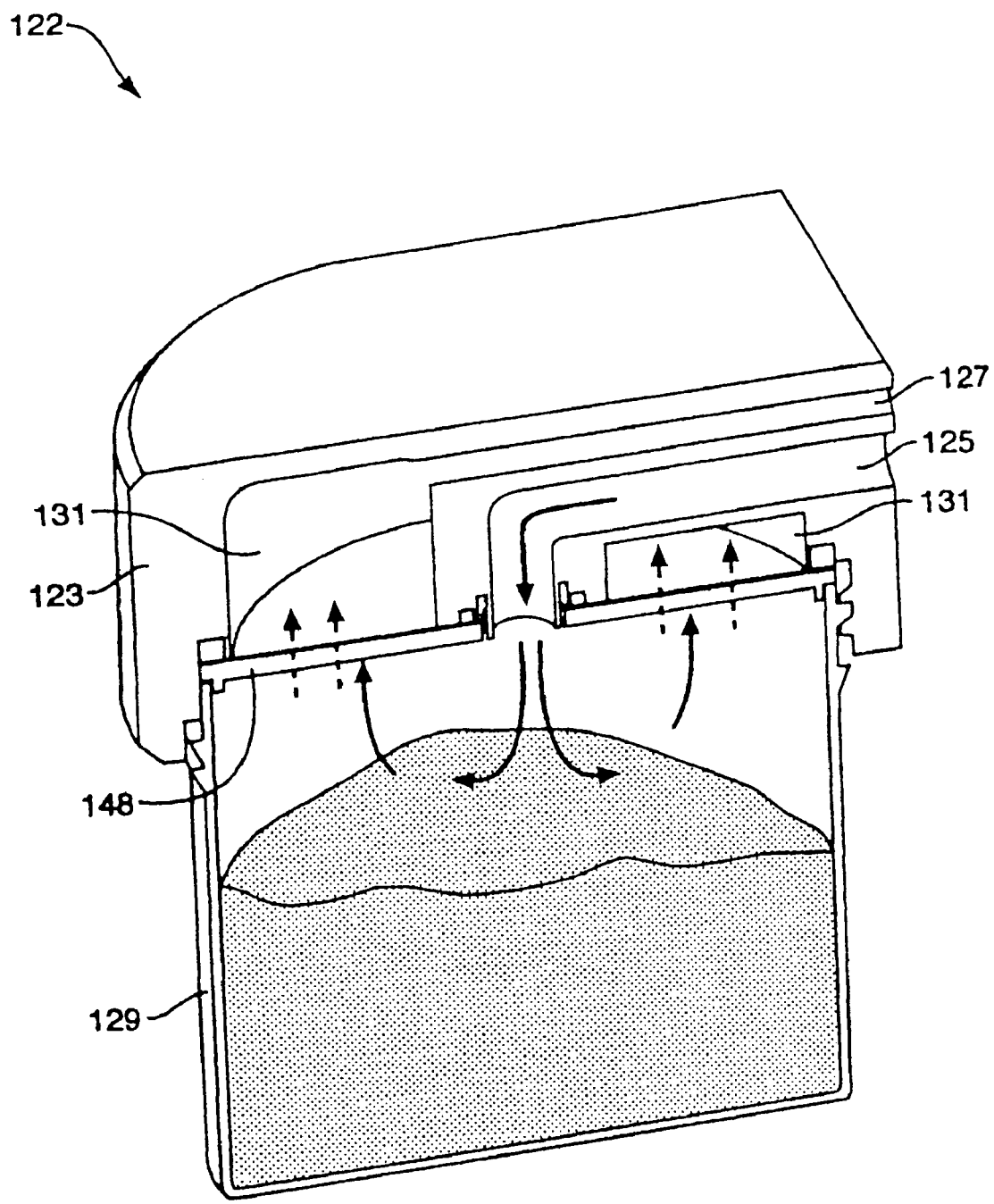
FIG. 11A illustrates a collection device utilized to hold waste debris after the abrading procedure in accordance with the present invention.

The abrasive within feeding chamber 136 then is directed through hand piece 118 to perform the desired abrasive operation on subject 20. During the actual abrading procedure, the abrasive abrades the skin causing waste debris and refuse that must be removed so as not to interfere with or contaminate the abraded surface. The pneumatic air supply, in this case vacuum generator 112, provides a vacuum in hand piece 118 that draws the waste refuse and debris away from the subject while at the same time performing surface abrasion. The waste refuse collects in abrasive collection device 122. Abrasive collection device 122 is shown in FIG. 11A, which is a cut-away perspective view of the abrasive collection device 122.

Collection device 122 includes a waste can receiver 123, which has an intake port 125 and a return port 127, a waste canister 129, and a filter 148. Waste can receiver 123 has a threaded seal in which to receive canister 129. Canister 129 collects the waste refuse during an abrasion procedure for later disposal. In the preferred embodiment, Canister 129 is identical to canister 116 used to feed the abrasive; however, this might not be the case in other embodiments. Once canister 116 is empty, it is removed and used to replace canister 129 once it is full, which is usually by the time canister 116 is empty. A cap threads onto canister 129 once it is full to seal the contents for proper disposal and to minimize any unnecessary contact with the refuse by the technician.

The waste refuse travels through intake port 125 to be deposited into canister 127. The air flows through filter 148 before exiting through return port 127, which couples to second filter 124 before being dispersed to ambient air. Although not mandatory for operation, use of second filter 124 is recommended to both remove any material untrapped by filter 148 and to act as a fail-safe particulate trap in the event filter 148 is either inadvertently left out of the system or is improperly installed. A return cavity 131 is disposed between filter 148 and return port 127 to keep the airflow from being unduly restricted during the filtering procedure.

Figure 11B:
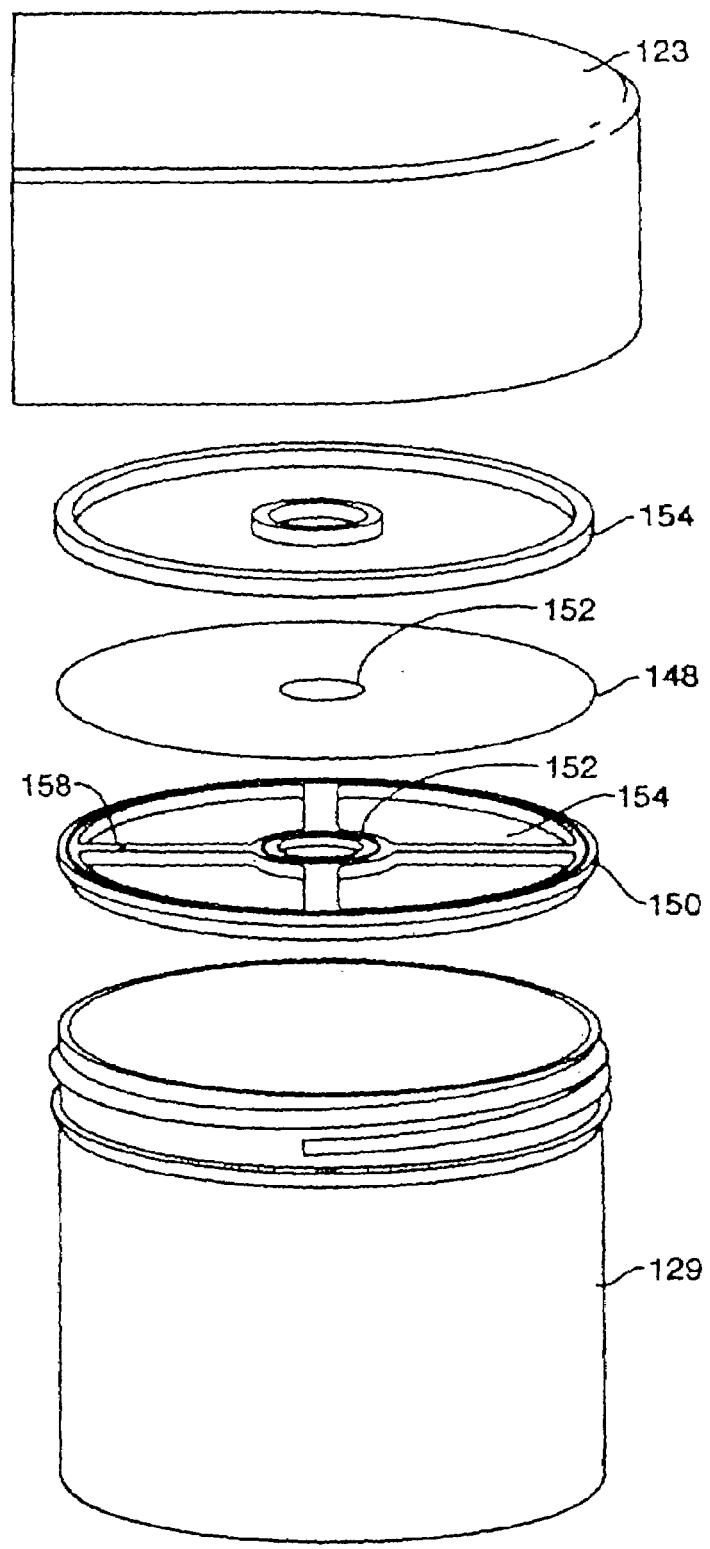
FIG. 11B depicts an exploded view of the collection device of FIG. 4A accordance with the present invention.

Referring to FIG. 11B, Filter 148 includes a support element 150, an intake aperture 152, through which the waste refuse material passes into canister 129, and filter apertures 154. The waste refuse material passes through aperture 152 into canister 129. The vacuum within device 122 then passes through filter 148 and underlying filter apertures 154, filter 148 preventing the refuse material from passing to chamber 131 to the vacuum generator 112.

Ring seals 154 are positioned within receiver 123 and superior to filter 148 about both its outer perimeter and its inner perimeter about aperture 152 to provide compliant sealing surfaces. Additionally, inner and outer crimping features 158 are provided upon the top surface of support element 150 and are positioned beneath ring seals 154. The crimping features 158 can be a one or a series of adjacent concentric ridges that press into filter 148 to hold it in place against compliant ring seals 154 and to provide an anti-bleed seal.

Filter 148 provides a larger surface area than filters utilized in the collection of the waste debris of the prior art. Further, the surface area is also such that the airflow is not inhibited since air flow return port 127 is removed from being immediately adjacent the filter 148. Also, in one embodiment filter 148 is disposable and inexpensive so it can be replaced between treatments, thus eliminating the progressive clogging experienced with durable-use filters or cleaning steps typically required in the prior art.

It is also intended that the discharge tube between hand piece 118 and waste collection or accumulation device 122 be easily removable so that it can be cleaned between sessions to prevent contamination and unsanitary build up of the waste debris residue that remains in the tube. Each end of the discharge tube can be pressure fitted or coupled via connectors that provide a suitable vacuum seal to prevent air bleeding into the system and lowering airflow inadvertently.

Figures 12A, 12B:
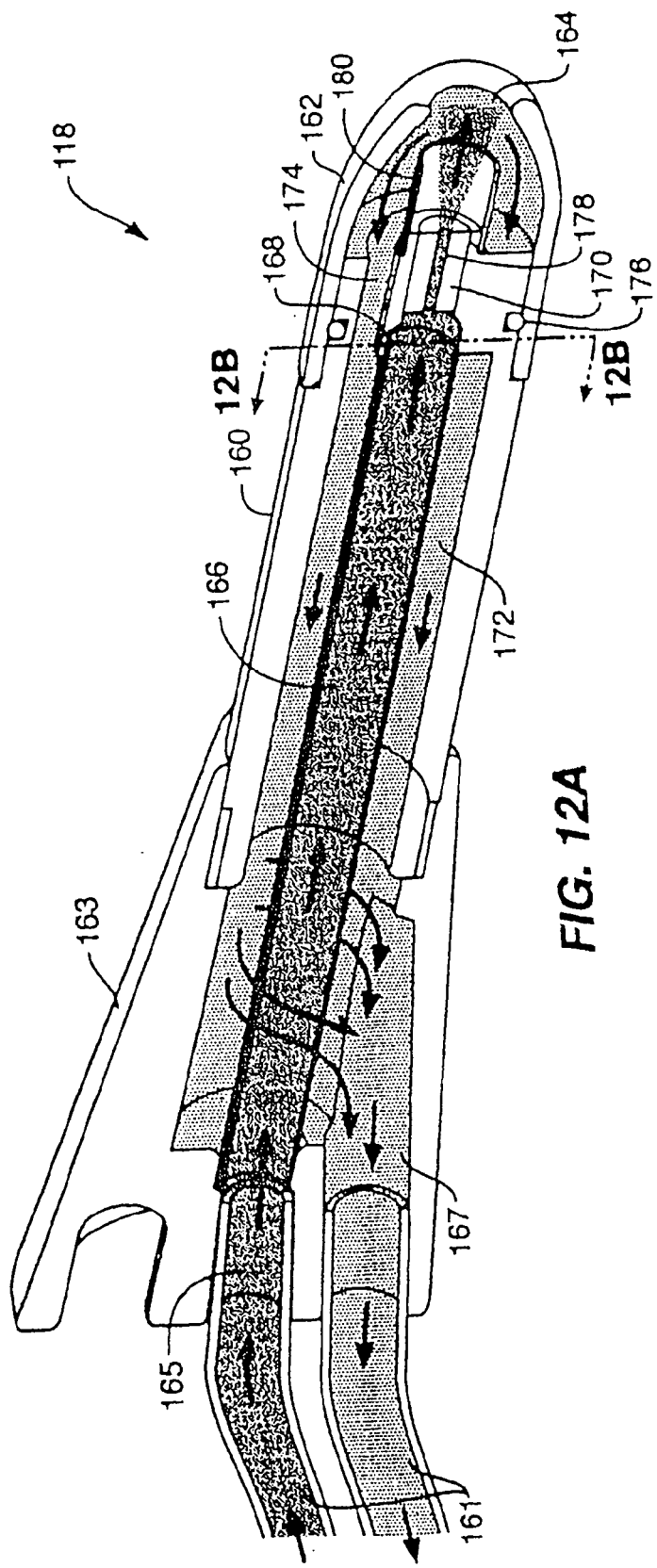
FIG. 12A illustrates a cross-sectional perspective view the hand piece utilized with the dermabrasion apparatus of FIG. 2 in accordance with the present invention.
FIG. 12B illustrates a cross-sectional view along the 5B direction in FIG. 5A.

Hand piece 118 is shown in cross-sectional detail in FIG. 12A, which is a cross-sectional perspective view along the longitudinal center axis. Hand piece 118 is assembled in a plurality of parts. There are three main portions assembled from these parts, which include hand piece body 160, tip 162, and end portion 163. Tip 162 friction mates with one end of hand piece body 160, while the other end of hand piece body 160 couples to end portion 163. End portion 163 is flared shaped for operator comfort during an abrasion session and so it will be retained in a retaining member on the vacuum apparatus 112 of FIG. 9. End portion 163 has two apertures, a supply aperture 165 and a return aperture 167. The supply aperture 165 couples to feeding device 114 to receive the abrasive for the treatment. The return aperture 167 couples to the waste collection device 122 to transport the used abrasive and debris from the dermabrasion treatment to device 122. Plastic flexible tubes 161 are used in one embodiment where the tubes have a slightly greater diameter than the apertures so that they friction fit there in and extend at least one-half inch to provide an adequate barrier from air bleed at these connection points.

A center channel 166 is positioned within a recess of end portion 165 to connect with the supply aperture 165. Center channel 166 fits within body 162 until it engages an output aperture 168. Within the output aperture 168 is fitted a nozzle 170 that concentrates the abrasive just prior to abrading a selected surface and causes the abrasive to stream in a fan cone pattern, but with a tight radius for control. Surrounding center channel 166 is a return channel 172, which is larger than and concentric with channel 166. The larger diameter of channel 168 allows for a sufficient air flow that the waste debris is readily transported to the refuse accumulation device 122 without clogging or hindering the air flow of the supply abrasive. Surrounding aperture 168 are a plurality of intake apertures 174. The intake apertures open to channel 168 and allow the waste debris to be removed from within tip 162 during treatment.

Tip 162 is generally bell-shaped and includes an abrasive aperture 164. Abrasive aperture 164 contacts the surface to be treated and closes the pneumatic circuit to draw abrasive through the system and abrade the surface. Abrasive aperture 164 is approximately one-quarter inch in diameter and is applied to the subject, such as a patient's skin, during the abrasive procedure. An O-ring 176 is fitted within a groove 174 about the end of body 160 to which tip 162 fits. O-ring 176 serves to proved a tight seal against air-bleed within the airflow. The O-ring 176 is flexible and pliant, typically made from rubber, neoprene, silicone, plastic, or any like and compatible substance.

Nozzle 170 is generally cylindrical in shape with an aperture 178 along its center axis. Nozzle 170 is made of a hard, durable substance that withstands the abrading process of the abrasive as the abrasive hits the nozzle with full force. These materials can comprise, but are not limited to, stainless steel, ceramic, aluminum, tungsten carbide, and other comparable substances. A nose tube 180 is optionally mounted to the operational end of body 160 and is concentric with nozzle 170. Nose tube 180 is generally cylindrical and helps divert the waste debris away from the abrasive during an abrading procedure while protecting the incoming abrasive steam from flow aberrations.

Since the hand piece 118 can be readily disassembled, it can be taken apart and thoroughly cleaned to avoid contamination and other health risks possible in performing dermabrasion and removing the waste debris. Further, the parts to hand piece 118 can be made of inexpensive, yet durable materials that allow for the hand piece, in part or in total, to be disposable.

The jet path of the abrasive may fan out enough to strike the inner wall of tip 162 at the margins of aperture 169. Since the abrasive is traveling at a high rate of speed, it causes the inner wall of tip 62 to wear away. Additionally, the act of scanning tip 162 across abrasive-covered skin will serve to abrade the outer surface of tip 162 near aperture 169. Accordingly, tip 162 is made compact and inexpensive so that it can be easily replaced and disposed of, preferably after each treatment. Suitable materials used to make tip 162 include polycarbonate, other plastics and resins, and other suitable substances with similar properties, specifically high-speed/low-cost moldability.

There are synergistic effects in combining the massage treatment provided by the massage device of FIGS. 1–7 with the dermabrasion treatment provided by the dermabrasion system of FIGS. 8–12. Both systems utilize the same negative pressure or vacuum source for operation. The dermabrasion system itself does provide a superficial massage benefit to the surface of the skin; however, the massage benefit is very limited and the deep tissue massage achieved by the massage device in accordance with the present invention provides greater benefits. The benefits of performing the deep tissue massage in conjunction with the dermabrasion treatment are that deep tissue massage provides stimulation of the blood vessels and the underlying skin cells to regrow the abraded skin. The treatments can be performed in either order so long as care is taken in not abrading the skin too deeply to the point of exposing surface blood vessels. This treatment is desirable for delicate skin surfaces such as the face. The treatment abrades away dead skin tissue as well as stimulates deep tissue regeneration to grow back the skin as well as to fill in crevices formed by wrinkles or scars or other blemishes. The results are toned and renewed skin.

The present invention may be embodied in other specific forms without departing from its spirit or essential characteristics. The described embodiments are to be considered in all respects only as illustrative and not restrictive. For example, the abrasion system can be scaled to other commercial and industrial uses such as sand blasting, deposition delivery to a surface, and is not intended to be limited to just dermabrasion systems as disclosed. Further, a second vacuum hose can be added so that both the massage unit and the dermabrasion unit can operate simultaneously on either the same rent subjects. The scope of the invention is, therefore, indicated by the appended claims, rather than by the foregoing description. All changes which come within the meaning and range of equivalency of the claims are to be embraced within their scope.

What is claimed is:

1. An abrasion and massage apparatus for use on a patient, the apparatus comprising:

a vacuum generator;

a massage head coupled to the vacuum generator, the massage head in combination with the vacuum generator comprising:
  means for generating an area of negative pressure along a dermal surface of the patient; and
  means for applying positive pressure to the patient's skin that is undergoing the negative pressure; and
a dermabrasion system comprising:
  a dermabrasion hand piece coupled to the vacuum generator and configured to deliver an abrasive material;
  an abrasive material supply device;
  a receiving channel coupled to the supply device;
  a feeding chamber coupled to the receiving channel;
  a delivery channel coupled to the feeding chamber and to the dermabrasion hand piece; and
  a waste retrieval holding device, coupled to the dermabrasion hand piece, to collect and store the delivered abrasive material and waste debris after treatment.

2. The apparatus according to claim 1 wherein the abrasive material supply device gravity feeds the abrasive material to the feeding chamber.

3. The apparatus according to claim 1 wherein the receiving channel extends within the feeding chamber and controls the amount of abrasive material filling the feeding chamber.

4. The apparatus according to claim 1 wherein the feeding chamber comprises a top, a bottom, and generally inwardly sloped walls from the top to the bottom.

5. The apparatus according to claim 4 wherein the abrasive material supply device comprises generally inwardly sloping walls with an opening at the bottom coupled to the receiving channel.

6. The apparatus according to claim 1 wherein the delivery channel connects to an inverted generally funnel-shaped collector channel used to receive abrasive material within the feeding chamber and to direct the abrasive material to the delivery channel.

7. The apparatus according to claim 1 wherein the waste retrieval holding device comprises a filter.

8. The apparatus according to claim 1 wherein the dermabrasion hand piece comprises a supply aperture and a return aperture.

9. The apparatus according to claim 1 wherein the dermabrasion hand piece comprises a removable tip that contacts a dermal surface of the patient that is to be abraded.

10. A dermal abrasion and massage apparatus comprising:
  a vacuum generator configured for use in dermal abrasion and massage of a patient, the vacuum generator coupled to:
    a dermabrasion hand piece of a dermal abrasion system, the dermal abrasion system further comprising:
      a feeding chamber that has a generally funnel-shaped portion that receives an abrasive material from a source for use in the dermal abrasion;
      a receiving channel that limits the amount of abrasive material supplied to the feeding chamber;
      an intake aperture, connected to a base of the feeding chamber to receive means for displacing the abrasive material in a substantially vertical direction; and
      a delivery channel, placed above the feeding chamber to receive the displaced abrasive, and coupled to the dermabrasion hand piece; and
    a massage head of a massage system, the massage head defining a cavity and an opening to the cavity, wherein the massage system is configured to create a negative pressure within the cavity, wherein the massage head includes a first contact surface to the patient, and wherein the massage system further includes a post coupled to the massage head and positioned within the cavity, the post being static relative to the massage head during massage and having a second contact surface to the patient.

11. The apparatus according to claim 10 further comprising a generally funnel-shaped supply device, positioned above the feeding chamber and connected to the receiving channel.

12. The apparatus according to claim 10 wherein the apparatus is pneumatically driven.

13. The apparatus according to claim 10 wherein the funnel-shape of the feeding chamber forms an arc ranging approximately 40 degrees to 90 degrees.

14. The apparatus according to claim 10 wherein the funnel-shape of the feeding chamber forms an arc of generally 60 degrees.

15. The apparatus according to claim 12 further comprising an airflow regulator, coupled to the delivery channel, to regulate a flow of the abrasive material during operation.

16. The apparatus according to claim 10 wherein the delivery channel comprises an inverted funnel-shaped opening within the feeding chamber.

17. The apparatus according to claim 10 further comprising a transition chamber disposed between the source and the feeding chamber.

18. A dermabrasion and massage apparatus comprising:
  a vacuum generator;
  a massage head defining a cavity and coupled to the vacuum generator, wherein the massage head in combination with the vacuum generator is configured to provide an effleurage-like massage; and
  dermabrasion system comprising (i) a dermabrasion hand piece coupled to the vacuum generator and configured to deliver an abrasive material, (ii) an abrasive material supply device, (iii) a receiving channel coupled to the supply device, (iv) a feeding chamber coupled to the receiving channel, (v) a delivery channel coupled to the feeding chamber and to the dermabrasion hand piece, and (vi) a waste debris receiving device coupled to the dermabrasion hand piece and to the vacuum generator to collect and store waste debris and the delivered abrasive material after treatment.

19. The dermabrasion and massage apparatus according to claim 18, wherein the dermabrasion hand piece comprises a body having a first end, a second end, a delivery aperture communicatively coupled to the first end and to the delivery channel, a retrieval aperture communicatively coupled to the first end and to a retrieval channel, and a dermabrasion tip that removably mounts to the first end of the hand piece body.

20. The dermabrasion and massage apparatus according to claim 19 wherein the delivery channel includes an intake aperture and the retrieval channel includes an outlet aperture, both intake and outlet apertures positioned at the second end of the body with the intake aperture concentric with the delivery channel and the outlet aperture offset from the intake aperture.

21. The dermabrasion and massage apparatus according to claim 20 wherein the tip is generally dome-shaped.

22. The dermabrasion and massage apparatus according to claim 20 wherein the delivery channel comprises a hollow tube coupled between the first and second ends of the hand piece body.

23. The dermabrasion and massage apparatus according to claim 22 wherein the hollow tube is removable.

24. The dermabrasion and massage apparatus according to claim 23 wherein the hand piece body comprises a middle portion and an end portion removably connected to the middle portion.

25. The dermabrasion and massage apparatus according to claim 20 further comprising a nozzle placed at the first end of the hand piece body adjacent the delivery aperture with an opening through which the abrasive material passes.

26. The dermabrasion and massage apparatus according to claim 20 further comprising a nose tube, concentric with the delivery channel and removably attached to the first end of the hand piece body.

27. The dermabrasion and massage apparatus according to claim 20 further comprising an O-ring mounted on the first end of the body.

28. A dermabrasion and massage device, the device comprising:
    a vacuum generator configured to collect waste debris and to provide a negative pressure that is used in providing a massage;
    a massage head of a massage system that includes the vacuum generator, the massage head defining a cavity and an opening to the cavity, wherein the massage system is configured to create a negative pressure within the cavity that is used in providing the massage;
    a dermabrasion hand piece of a dermal abrasion system that includes the vacuum generator, the dermal abrasion system further comprising:
        a feeding chamber that has a generally funnel-shaped portion that receives an abrasive material from a source for use in the dermal abrasion;
        a receiving channel that limits the amount of abrasive material supplied to the feeding chamber;
        an intake aperture, connected to a base of the feeding chamber to receive means for displacing the abrasive material in a substantially vertical direction;
        a delivery channel, placed above the feeding chamber to receive the displaced abrasive, and coupled to the dermabrasion hand piece;
        a waste can receiver coupled to the dermabrasion hand piece;
        a waste canister removably coupled to the waste can receiver at an open end of the waste canister; and
        a filter disposed between the waste can receiver and the waste canister such that an intake port of the dermabrasion system passes through the filter and the filter prevents waste debris from exiting the waste canister through a return port.

29. The device according to claim 28 further comprising a filter frame configured to support and retain the filter in position between the waste can receiver and the waste canister and having an aperture through which the intake port passes.

30. The device according to claim 28 further comprising pliable retention prongs to secure the filter between the waste canister and the waste can receiver to prevent air-bleeding at the filter location.

31. The device according to claim 29 wherein the filter is removable.

32. The device according to claim 29 wherein the waste canister further comprises a removable lid to seal the waste canister upon removal from the waste can receiver.

33. The device according to claim 29 wherein the filter comprises a fabric having pores that prevent the waste debris from passing therethrough.

34. An apparatus for selectively performing dermabrasion or massaging, comprising:
    a vacuum generator;
    a massage device, coupled to and operable by the vacuum generator, comprising:
        a massage head; and
        a handle, coupled to the massage head; and
    a dermabrasion device, coupled to and operable by the vacuum generator, comprising:
        a dermabrasion hand piece for delivery and retrieval of an abrasive material;
        an abrasive material source device;
        a dermabrasive handling device, coupled to the source device and to the hand piece; and
        a waste debris receiving device, coupled to the hand piece, to collect and store waste debris and the delivered abrasive material after treatment.

35. The apparatus according to claim 34 wherein the dermabrasive handling device gravity feeds the abrasive material to a feeding chamber.

36. The apparatus according to claim 35 wherein a receiving channel extends within the feeding chamber a sufficient distance to control an amount of abrasive material entering the feeding chamber.

37. The apparatus according to claim 35 wherein feeding chamber comprises a generally funnel shaped chamber in which the abrasive material is lofted during operation.

38. The apparatus according to claim 35 wherein a delivery channel connects to an inverted generally funnel-shaped collector channel to receive the abrasive material within the feeding chamber and direct it to the delivery channel.

39. The apparatus claimed in claim 34 wherein the massage head comprises one or more substantially flat contact surfaces to enable the massage device to deliver an effleurage-like massage.

40. The apparatus as claimed in claim 34 wherein the massage head comprises a rim that has a substantially flat contact surface and enables a substantially air tight seal.

41. A method for treating a skin surface comprising:
    actuating a vacuum generator to selectively operate (i) a massage system, and (ii) a dermabrasion system;
    using the vacuum generator in combination with the massage system to deliver a deep tissue massage on a patient across a section of the patient's skin; and
    using the vacuum generator in combination with the dermabrasion system to deliver a dermabrasion treatment across the section of the patient's skin.

42. The method for treating a skin surface according to claim 41 wherein the delivery of the deep tissue massage comprises:
    using the vacuum generator in combination with a massage head to generate an area of negative pressure on the patient's skin surface, the area of negative pressure defined by a perimeter of positive pressure; and
    applying a second positive pressure radially interior to the perimeter.

43. The method for treating a skin surface according to claim 41 wherein the delivery of the dermabrasion treatment comprises:
    drawing abrasive material from the dermabrasion system to abrade the skin surface; and
    using negative pressure from the vacuum generator to collect the drawn abrasive material and abraded skin debris to a refuse container.

* * * * *